United States Patent
Banerjee et al.

(12)

(10) Patent No.: US 6,261,806 B1
(45) Date of Patent: Jul. 17, 2001

(54) MOLECULAR SEQUENCE OF SWINE RETROVIRUS AND METHODS OF USE

(75) Inventors: Papia T. Banerjee, Lexington; Clive Patience, Charlestown; Goran K. Andersson, Newton, all of MA (US)

(73) Assignee: BioTransplant, Inc., Charlestown, MA (US)

( * ) Notice: Subject to any disclaimer, the term of this patent is extended or adjusted under 35 U.S.C. 154(b) by 0 days.

(21) Appl. No.: 09/376,781

(22) Filed: Aug. 18, 1999

Related U.S. Application Data

(60) Provisional application No. 60/097,015, filed on Aug. 18, 1998.

(51) Int. Cl.[7] .......................... A61K 39/21; C07H 21/04; C07K 14/15; C12N 5/16; C12N 7/00
(52) U.S. Cl. .................. 435/69.3; 424/139.1; 424/147.1; 424/159.1; 424/186.1; 424/187.1; 424/207.1; 435/235.1; 435/320.1; 435/325; 514/44; 530/300; 530/388.35; 536/23.72
(58) Field of Search .............................. 424/139.1, 147.1, 424/159.1, 186.1, 187.1, 207.1; 435/69.3, 235.1, 320.1, 325; 514/44; 530/300, 388.35; 536/23.72

(56) References Cited

U.S. PATENT DOCUMENTS 5,140,105   8/1992   Ohno .

FOREIGN PATENT DOCUMENTS

WO 97/21836   6/1997   (WO) .
WO 97/40167   10/1997   (WO) .

OTHER PUBLICATIONS

Takeuchi, et al., "Host Range and Interference Studies of Three Classes of Pig Endogenous Retrovirus", Journal of Virology, pp. 9986–9991 (1998)—XP–002126426.

Akiyoshi, et al., "Identification of a Full–Length cDNA for an Endogenous Retrovirus of Miniature Swine", Journal of Virology, pp. 4503–4507 (May 1998)—XP–002126425.

Patience, Clive, "Infection of Human Cells by an Endogenous Retrovirus of Pigs", *Nature Medicine*, vol. 3, pp. 282–286 (Mar. 1997).

Tissier et al. "Two Sets of Human–Tropic Pig Retrovirus", *Nature Medicine*, vol. 389, pp. 681–682 (Oct. 1997).

*Primary Examiner*—Phuong T. Bui
(74) *Attorney, Agent, or Firm*—Elliot M. Olstein; Alan J. Grant

(57) ABSTRACT

This invention relates to newly identified polynucleotides, polypeptides encoded by such polynucleotides, the use of such polynucleotides and polypeptides, as well as the production of such polynucleotides and polypeptides. More particularly, the polypeptides of the present invention are PERV-D env polypeptides. The invention also relates to detecting the presence of a porcine retrovirus in tissue comprising such polypeptides or polynucleotides that encode the polypeptides.

15 Claims, 29 Drawing Sheets

FIGURE 1

```
CCAACCTCTC AGCAGGATAG GGTAAGCTTT TCTTATGTCA ACCCCAATAA      50
CCACCGGACC TGGAAAACGT CATACAGGTA CCATTCTGGG TGTTTTCCCT     100
CAGACCTAGA TTATCTTAAA ATAAGTTTCA CCGAAAAAAA AAAACAAGAA     150
AATATCCTAA AATGGATAAA TGGTATGTCC TGGGGAATAA TATATTATAC     200
AGGTTGGGAC AGACAACCAG GCTCCATTCT AACCATCCGA CTTAAAATAA     250
GCCAGCTGGA GCCTCCAATG GCTAT                                275
```

FIGURE 2

```
PTSQQDRVSF SYVNPNNHRT WKTSYRYHSG CFPSDLDYLK ISFTEKKKQE      50
NILKWINGMS WGIIYYTGWD RQPGSILTIR LKISQLEPPM A              91
```

FIGURE 3A

```
PERV-D  ---------- ----------  ----------  ----------  ----------  ----------
PoEV    MHPTLSRRHL PTRGGEPKRL  RIPLSFASIA  WFLTLTITPQ  ASSKRLIDSS  50
PERV-B  MHPTLSWRHL PTRGGEPKRL  RIPLSFASIA  WFLTLTITPQ  ASSKRLIDSS  50
PERV-A  MHPTLSRRHL PIRGGKPKRL  KIPLSFASIA  WFLTLSITPQ  VNGKRLVDSP  50
PERV-C  MHPTLNRRHL PIRGGKPKRL  KIPLSFASIA  WFLTLSITSQ  TNGMRIGDSL  50

PERV-D  ---------- ----------  ----------  ----------  ----------  ---
PoEV    NPHRPLSLTW LIIDPDTGVT  VNSTRGVAPR  GTWWPELHFC  LRLINPAV--  98
PERV-B  NPHRPLSLTW LIIDPDTGVT  VNSTRGVAPR  GTWWPELHFC  LRLINPAV--  98
PERV-A  NSHKPLSLTW LLTDSGTGIN  INSTQGEAPL  GTWWPELYVC  LRSVIPGLND  100
PERV-C  NSHKPLSLTW LITDSGTGIN  INNTQGEAPL  GTWWPDLYVC  LRSVIPSL--  98

PERV-D  ---------- ----------  ----------  ----------  -------P    1
PoEV    KSTPPNLVRS YGFYCCPG-T  EKEKYCGGSG  ESFCRRWSCV  TSNDGDWKWP  147
PERV-B  KSTPPNLVRS YGFYCCPG-T  EKEKYCGGSG  ESFCRRWSCV  TSNDGDWKWP  147
PERV-A  QATPPDVLRA YGFYVCPGPP  NNEEYCGNPQ  DFFCKQWSCI  TSNDGNWKWP  150
PERV-C  -TSPPDILHA HGFYVCPGPP  NNGKHCGNPR  DFFCKQWNCV  TSNDGYWKWP  147
```

FIGURE 3B

| | | | | | | |
|---|---|---|---|---|---|---|
| PERV-D | TSQQDRVSFS | YVNPN----- | -----NHRTWK- | ----- | ----TSYR | YH-SGCFPSD | 35 |
| PoEV | ISLQDRVKFS | FVNS------ | ---GPGKYK- | ----- | -MKLYK | DK--SCSPSD | 181 |
| PERV-B | ISLQDRVKFS | FVNS------ | ---GPGKYK- | ----- | -VMKLYK | DK--SCSPSD | 181 |
| PERV-A | VSQQDRVSYS | FVNNPTSYNQ | FNYGHGRWKD | WQQRVQKDVR | NKQISCHSLD | | 200 |
| PERV-C | TSQQDRVSFS | YVNTYT---- | ---SSGQFN- | ----- | -YLTWIR | TGSPKCSPSD | 185 |

| | | | | | | |
|---|---|---|---|---|---|---|
| PERV-D | LDYLKISFTE | KK--KQENIL | KWINGMSWGI | IYYTGWDRQP | GSILTIRLKI | | 83 |
| PoEV | LDYLKISFTE | RKTGKYSKVD | KWYE-L--GN | SFLLYGG-GA | GSTLTIRLRI | | 227 |
| PERV-B | LDYLKISFTE | K--GKQENIQ | KWINGMSWGI | VFYKYGG-GA | GSTLTIRLRI | | 228 |
| PERV-A | LDYLKISFTE | K--GKQENIQ | KWVNGISWGI | VYYGGSGRKK | GSVLTIRLRI | | 248 |
| PERV-C | LDYLKISFTE | K--GKQENIL | KWVNGMSWGM | VYYGGSGKQP | GSILTIRLKI | | 233 |

| | | | | | | |
|---|---|---|---|---|---|---|
| PERV-D | S-QLEPPMA- | ---------- | ---------- | ---------- | ---------- | | 91 |
| PoEV | ETGTEPPVAM | GPDKVLAEQG | PPALEPPHNL | PVPQLTSLRP | DITQPPSNST | | 277 |
| PERV-B | ETGTEPPVAV | GPDKVLAEQG | PPALEPPHNL | PVPQLTSLRP | DITQPPSNGT | | 278 |
| PERV-A | ETQMEPPVAI | GPNKGLAEQG | PPIQEQ---- | ------RP | SPNPSDYNTT | | 286 |
| PERV-C | N-QLEPPMAI | GPNTVLTGQR | PPTQGP---- | ---------- | ---GPSSNIT | | 265 |

FIGURE 3C

| | | | | | | |
|---|---|---|---|---|---|---|
| PERV-D | ---------- | ---------- | ---------- | ---------- | ---------- | 91 |
| PoEV | TGLIPTNTPR | NSPGVPVKTG | QRLFSLIQGA | FQAINSTDPD | ATSSCWLCLS | 327 |
| PERV-B | TGLIPTNTPR | NSPGVPVKTG | QRLFSLIQGA | FQAINSTDPD | ATSSCWLCLS | 328 |
| PERV-A | SGSVPTE--- | --PNITIKTG | AKLFSLIQGA | FQALNSTTPE | ATSSCWLCLA | 331 |
| PERV-C | SGSDPTE--- | --SSSTTKMG | AKLFSLIQGA | FQALNSTTPE | ATSSCWLCLA | 310 |
| | | | | | | |
| PERV-D | ---------- | ---------- | ---------- | ---------- | ---------- | 91 |
| PoEV | SGPPYYEGMA | KERKFNVTKE | HRNQCTWGSR | NKLTLTEVSG | KGTCIGKAPP | 377 |
| PERV-B | SGPPYYEGMA | KEGKFNVTKE | HRNQCTWGSR | NKLTLTEVSG | KGTCIGKAPP | 378 |
| PERV-A | SGPPYYEGMA | RGGKFNVTKE | HRDQCTWGSQ | NKLTLTEVSG | KGTCIGMVPP | 381 |
| PERV-C | SGPPYYEGMA | RRGKFNVTKE | HRDQCTWGSQ | NKLTLTEVSG | KGTCIGKVPP | 360 |
| | | | | | | |
| PERV-D | ---------- | ---------- | ---------- | ---------- | ---------- | 91 |
| PoEV | SHQHLCYSTV | VYEQASENQY | LVPGYNRWWA | CNTGLTPCVS | TSVFNQSKDF | 427 |
| PERV-B | SHQHLCYSTV | VYEQASENQY | LVPGYNRWWA | CNTGLTPCVS | TSVFNQSKDF | 428 |
| PERV-A | SHQHLCNHTE | AFNRTSESQY | LVPGYDRWWA | CNTGLTPCVS | TLVFNQTKDF | 431 |
| PERV-C | SHQHLCNHTE | AFNQTSESQY | LVPGYDRWWA | CNTGLTPCVS | TLVFNQTKDF | 410 |

FIGURE 3D

| | | | | | | |
|---|---|---|---|---|---|---|
| PERV-D | ---------- | ---------- | ---------- | ---------- | ---------- | 91 |
| PoEV   | CVMVQIVPRV | YHPEEVVLD  | EYDYRYNRPK | REPVSLTLAV | MLGLGTAVGV | 477 |
| PERV-B | CVMVQIVPRV | YHPEEVVLD  | EYDYRYNRPK | REPVSLTLAV | MLGLGTAVGV | 478 |
| PERV-A | CVMVQIVPRV | YYYPEKAVLD | EYDYRYNRPK | REPISLTLAV | MLGLGVAAGV | 481 |
| PERV-C | CIMVQIVPRV | YYYPEKAILD | EYDYRNHRQK | REPISLTLAV | MLGLGVAAGV | 460 |
| PERV-D | ---------- | ---------- | ---------- | ---------- | ---------- | 91 |
| PoEV   | GTGTAALITG | PQQLEKGLGE | LHAAMTEDLR | ALKESVSNLE | ESLTSLSEVV | 527 |
| PERV-B | GTGTAALITG | PQQLEKGLGE | LHAAMTEDLR | ALEESVSNLE | ESLTSLSEVV | 528 |
| PERV-A | GTGTAALITG | PQQLEKGLSN | LHRIVTEDLQ | ALEKSVSNLE | ESLTSLSEVV | 531 |
| PERV-C | GTGTAALVTG | PQQLETGLSN | LHRIVTEDLQ | ALEKSVSNLE | ESLTSLSEVV | 510 |
| PERV-D | ---------- | ---------- | ---------- | ---------- | ---------- | 91 |
| PoEV   | LQNRRGLDLL | FLREGGLCAA | LKEECCFYVD | HSGAIRDSMN | KLRKKLERRR | 577 |
| PERV-B | LQNRRGLDLL | FLREGGLCAA | LKEECCFYVD | HSGAIRDSMS | KLRERLERRR | 578 |
| PERV-A | LQNRRGLDLL | FLKEGGLCVA | LKEECCFYVD | HSGAIRDSMS | KLRERLERRR | 581 |
| PERV-C | LQNRRGLDLL | FLKEGGLCVA | LKEECCFYVD | HSGAIRDSMN | KLRERLEKRR | 560 |

FIGURE 3E

```
                                                                                            91
PERV-D  ------- -------  -------- --------  ---------- ----------
PoEV    REREADQGWF  EGWFNRSPWM  TTLLSALTGP  LVVLLLLLTV  GPCLINRFVA   627
PERV-B  REREADQGWF  EGWFNRSPWM  TTLLSALTGP  LVVLLLLLTV  GPCLINRFVA   628
PERV-A  REREADQGWF  EGWFNRSPWM  TTLLSALTGP  LVVLLLLLTV  GPCLINRFVA   631
PERV-C  REKETTQGWF  EGWFNRSLWL  ATLLSALTGP  LIVLLLLLTV  GPCIINKLIA   610

91
PERV-D  ---------- ----------  ---------- ----------
PoEV    FVRERVSAVQ  IMVLRQQYQG  LLSQGETDL                           656
PERV-B  FVRERVSAVQ  IMVLRQQYQG  LLSQGETDL                           657
PERV-A  FVRERVSAVQ  IMVLRQQYQG  LLSQGETDL                           660
PERV-C  FIRERISAVQ  IMVLRQQYQS  PSSR-EAGR                           638
```

FIGURE 4A1

```
Aligned sequences

PERV-D  -------G CCAACCTCT A-------- -------- --G--CAGG-         17
PERV A  CCCATAAACC CTTATCTCTC ACCTGGTTAC TTACTGACTC CGGTACAGGT    50

PERV-D  ----AT--   --------   AGGGTAAGCT  ---TT----   -------TC   33
PERV A  ATTAATATTA ACAGCACTCA AGGGAGGCT  CCCTTGGGGA  CCTGGTGGCC  100

PERV-D  T----TAT GTC-------   -------AA-  CCC-----C  AATAACCA--   54
PERV A  TGAATTATAT GTCTGCCTTC GATCAGTAAT CCCTGGTCTC AATGACCAGG   150

PERV-D  -------- --------   --------   --------   ---CC-GGA         59
PERV A  CCACACCCCC CGATGTACTC CGTGCTTACG GGTTTTACGT TTGCCCAGGA   200

PERV-D  CC-------  -------   ---TGGAAAA CGTCATACAG GTACCATTCT      88
PERV A  CCCCCAAATA ATGAAGAATA TTGTGGAAA- --------   --------        229
```

FIGURE 4A2

```
Aligned sequences

PERV-D  GGGTGTTTC CCTCAGACCT AGATTATCTT AAAATAAGTT TCACCGAAAA  138
PERV A  --------T CCTCAG---- -GATT-TCT- ---------- TT----G---  247

PERV-D  AAAAAAACAA GAAAATATCC TAAAATGGA- ---------- ----------  167
PERV A  --------T ----CAA G--------- ---AATGGAG CTGCATAACT TCTAATGATG  279

PERV-D  ----T--AA ATGGTATGTC CTGGGAATA ATATATTATA CAGGTTGGGA  210
PERV A  GGAATTGGAA ATGG------C CAG------- ---T-CTCT- CAG--CAAGA  311

PERV-D  CAGA-CAA-C CAGGCTCCAT TCTAACCATC C--------- ----------  239
PERV A  CAGAGTAAGT TACTCTTT-T GTTAACAATC CTACCAGTTA TAATCAATTT  360

PERV-D  ---------- ---------- ----GACT-- ---------- ----------  243
PERV A  AATTATGCC ATGGGAGATG GAAAGATTGG CAACAGCGGG TACAAAAGA  410

PERV-D  --TA--AAAT AAGCCAGCTG GAGCCTCCAA TGGCTAT              276
PERV A  TGTACGAAAT AAGC-AAAT- AAGCTGTCAA TTCGTTA              445
```

FIGURE 4B1

Mismatched nucleotides

```
PERV-D   -------- -------G .CA.C.... .:::..... ........:  17
PERV A   CCCATAAACC .TT.T.... ..CCTGGTTAC TTACTGACTC CG.TA....T  50

PERV-D   -------:.. ---------- .....T.A.. ...:.:.... ------T..  33
PERV A   ATTAAT..TA ACAGCACTCA ...G.G.... CCC..GGGGA CCTGGTGGC.  100

PERV-D   .:.....:.. ...:...... ...:...... ...A...:.. ---...:GG  54
PERV A   .GAATTA.... ...TGCCTTC GATCAGT..T ...TGGTCT. ...G....GG  150

PERV-D   ---------- ---------- ---------- ---------- ---:.:...  59
PERV A   CCACACCCCC CGATGTACTC CGTGCTTACG GGTTTACGT TTGC..A...  200

PERV-D   ..:...:... ---------- --:.....A CGTCATACAG GTACCATTCT  88
PERV A   ..CCCAAATA ATGAAGAATA TTG....... ---------- ----------  229

PERV-D   ---------- ---------- ....ACCT A....A....T AAAATAAG..  138
PERV A   GGGTGTTTTC ......T... .......... ...:...... .CACC.AAAA  247
```

FIGURE 4B2

Mismatched nucleotides

```
PERV-D  ------- AAAAAAA.. .AAAATATC. TAA....... ------- -------          167
PERV A  ------- -------- ----...... ........G CTGCATAACT TCTAATGATG      279

PERV-D  ------- -------- ....TATGT. .T.GGGAATA ATA.AT.A.A ...GTTGG..      210
PERV A  GGAAT.GG ........ ....A..... ------- ------- ...-C.C.-  ..--CAA..   300

PERV-D  ------- ....-C C.GG..CCA. TC.....C... ------- -------              239
PERV A  ....GT..GT T.CT..TT-. GT.....A... ------- .TACCAGTTA TAATCAATTT      359

PERV-D  ------- AATTATGGCC ATGGGAGATG GAAA..T.GG CAACAGCGGG TACAAAAAGA      243
PERV A  ------- -------- -------- ....C..... ------- -------               409

PERV-D  ------- ....:..... ....C.GC.G G...CTC.... .GGC.AT                  276
PERV A  TG..CG.. ........ ----...-. -..AA.- A...TGT... .TCG.TA             436
```

FIGURE 5A

```
Aligned sequences

PERV-D   GCCAACCTCT CAGCAGGATA GGGTAAGCTT TTCTTATGTC AACCCCAATA    50
PERV B   GCCGATCTCT CTCCAGGACC GGGTAAAATT CTCCTTTGTC AATTCC---G    47

PERV-D   ACCACCGGAC CTGGAAAACG -TCATAC-AG GT-ACCATTC TGGGTGTTTT    97
PERV B   GCCCGGGCAA GTACAAAGTG ATGAAACTAT ATAAAGATAA GAGCTGCTCC    97

PERV-D   CCCTCAGACC TAGATTATCT TAAAATAAGT TTCACCGAAA AAAAAAAACA   147
PERV B   CCATCAGACT TAGATTATCT AAAGATAAGT TTCACTGAAA AAGGAAAACA   147

PERV-D   AGAAAATATC CTAAAATGGA TAAATGGTAT GTCCTGGGGA ATAATATATT   197
PERV B   GGAAAATATT CAAAAGTGGA TAAATGGTAT GAGCTGGGGA ATAGTTTTTT   197

PERV-D   ATACAGGTTG GGACAGACAA CCAGGCTCCA TTCTAACCAT CCGACTTAAA   247
PERV B   ATAAA--TAT GG-CGGGGGA GCAGGGTCCA CTTTAACCAT TCGCCTTAGG   244

PERV-D   ATA-AGCC-- AGCTGGAGCC TCCAATGGCT AT                       276
PERV B   ATAGAGACGG GGACAGAACC CCCTGTGGCA GT                       276
```

FIGURE 5B

Mismatched nucleotides

```
PERV-D   ...A.C.....   .AG.....TA   .......GC..   T..T.A....   ..CC..AATA    50
PERV B   ...G.T....    .TC.....CC   ........AA.. C..C.T....   ..TT..---G    47

PERV-D   A..ACC.G.C  C.GG...AC.   -.C.T..-.GG  G..-.CC..TC  TG.G..T.TT    97
PERV B   G..CGG.C.A  G.AC...GT.   A.G.A..TT    A.A.AG..AA   GA.C..C.CC    97

PERV-D   ..C.........  .........  T..A.......  .........  ..C.....  ..AA......   147
PERV B   ..A........T  .........  A..G.......  .........  ......T.  ..GG......   147

PERV-D   A..........  ..C..T...A.  .........  .........  .TC.......  ..A.A.A..    197
PERV B   G..........  ..T..A...G.  .........  .........  .AG.......  ..G.T.T..    197

PERV-D   ...C.GG.TG   ..A.A.ACA.  C......C..  .........  T.C.......  C..A....AA   247
PERV B   ...A.--.AT   ..-.G.GGG.  G.........  .........  C.T.......  T..C....GG   244

PERV-D   ...:.C.--  A.CTG..G..  T..AA....T A.                                     276
PERV B   ...G..A.GG G.ACA..A..  C..TG....A G.                                     275
```

FIGURE 6A

Aligned Sequences

```
PERV-D  GCCAACCTCT CAGCAGGATA GGGTAAGCTT TTCTTATGTC AAC-------    43
PERV-C  GCCAACCTCT CAGCAGGATA GGGTAAGTTT TTCTTATGTC AACACCTATA    50

PERV-D  CC-------- -CAA--TAAC CACCGGACCT GGAAAACGTC ATACAGGTAC    82
PERV-C  CCAGCTCTGG ACAATTAAT  TACCTGACCT GGATTA-G-- A-ACTGGAAG    96

PERV-D  CATTCTGGGT GTTTCCCTC  AGACCTAGAT TATCTTAAAA TAAGTTTCAC   132
PERV-C  C--CCCAAGT GCTCTCCTTC AGACCTAGAT TACCTAAAAA TAAGTTTCAC   144

PERV-D  CGAAAAAAAA AAACAAGAAA ATATCCTAAA ATGGATAAAT GGTATGTCCT   182
PERV-C  TGAGAAAGGA AAACAAGAAA ATATCCTAAA ATGGGTAAAT GGTATGTCTT   194

PERV-D  GGGGAATAAT ATATTATACA GGTTGGGACA GACAACCAGG CTCCATTCTA   232
PERV-C  GGGGAATGGT ATATTATGGA GGCTCGGGTA AACAACCAGG CTCCATTCTA   244

PERV-D  ACCATCCGAC TTAAAATAAG CCAGCTGGAG CCTCCAATGG CTAT          276
PERV-C  ACTATTCGCC TCAAAATAAA CCAGCTGGAG CCTCCAATGG CTAT          288
```

FIGURE 6B

Mismatched nucleotides

```
PERV-D  ..............  ..............  ..............  ..C........   43
PERV-C  ..............  ..............  ..............  ..T........   50

PERV-D  .------......  ....CC...G...  ..............  ..AA.C.TC  T.A..T.C   82
PERV-C  ..AGCTCTGG A...TT...T T...  ..............  ..TT.---  -..T.A.G   96

PERV-D  .ATT.TGG..  .T.T...C..  ..............  ..T.T......  ..........   132
PERV-C  .--C.CAA..  .C.C...T..  ..............  ..C.A......  ..........   144

PERV-D  C..A...AA.  ..............  ..............  ....A......  ..C......   182
PERV-C  T..G...GG.  ..............  ..............  ....G......  ..T......   194

PERV-D  ......AA..  .......AC.  ..T.G..AC. G......  ..........  ..........   232
PERV-C  ......GG..  .......GG.  ..C.C..GT. A......  ..........  ..........   244

PERV-D  ..C..C..A.  .T........  ..............  ..........  ..........   276
PERV-C  ..T..T..C.  .C........  ..............  ..........  ..........   288
```

FIGURE 7A

Aligned sequences

```
PERV-D       GCCAACCTCT CAGCAGGATA GGGTAAGCTT TTCTTATGTC AACCCCAATA    50
WO 97/40167  GCCGATCTCT CTCCAGGACC GGGTAAAATT CTCCTTTGTC AATTCC---G    47

PERV-D       ACCACCGGAC CTGGAAAACG -TCATAC-AG GT-ACCATTC TGGGTGTTTT    97
WO 97/40167  GCCCGGGCAA GTACAAAATG ATGAAACTAT ATAAAGATAA GAGCTGCTCC    97

PERV-D       CCCTCAGACC TAGATTATCT TAAAATAAGT TTCACCGAAA AAAAAAAACA   147
WO 97/40167  CCATCAGACT TAGATTATCT AAAGATAAGT TTCACTGAAA GGAAAA--CA   145

PERV-D       AGAAAATATC CTAAAATGGA TAAATGGTAT GTCCTGGGGA ATA---ATAT   194
WO 97/40167  GGAAAATATT CAAAAGTGAA TAAATGGTAT GAGCTGGGGA ATAGTTTTT    195

PERV-D       ATTATACAGG TTGGACAGA CAACCAGGCT CCATTCTAAC CATCCGACTT   244
WO 97/40167  ATTATAT-GG CGGGG---G- --AGCAGGGT CCACTTTAAC CATTCGCCTT   238

PERV-D       AAAATA-AGC CAG---CTGG AGCCTC---- -CAATGGCTA T            276
WO 97/40167  AGGATAGAGA CGGGGACAGA ACCCCCTGTG GCAATGG-GA C            278
```

FIGURE 7B

Mismatched nucleotides

```
PERV-D       ...A.C.....  .AG.....TA  ........GC..  T..T.A....  ..CC..AATA  50
WO 97/40167  ...G.T.....  .TC.....CC  ........AA..  C..C.T....  ..TT..---G  47

PERV-D       A..ACC.G.C  C.GG.....C.  -.C.T...-.G  G..-.CC..TC  TG.G..T.TT  97
WO 97/40167  G..CGG.C.A  G.AC.....T.  A.G.A.T.T    A.A.AG..AA  GA.C..C.CC  97

PERV-D       ..C.......C  ..........  T..A......  .......C....  AA.....AA..  147
WO 97/40167  ..A.......T  ..........  A..G......  .......T....  GG.....--..  145

PERV-D       A.........C  T...A.....  ..........  .TC.......  ...---A.A.  194
WO 97/40167  G.........T  .A...G....  ..........  .AG.......  ...GTTT.T.  195

PERV-D       ........CA..  TT...ACA.A  CA.C.....C.  .T.C......  ..C..A....  244
WO 97/40167  ........T-..  CG...-.---  --.G.....G.  .CT.......  ..T..C....  238

PERV-D       .AA....C  .A.---.T.G  .G..T----  -.....CT.  T  276
WO 97/40167  .GG....G.A  .G.GGA.A.A  .C..C.TGTG  G......-G.  C  278
```

FIGURE 8

```
CACCAACGGC TGTGAAAGTC GAAAAAATCT CCACCTAGAT CCATACATCC        50
CACGTTAAGC CGGCGCCACC TCCTGATTCA GGGTGAAAAG CCAAAAAGAC       100
TAAAAATCCC CTTAAGCTTC GCCTCCATCA CATGGTTCCT TACTCTGTCA       150
ATAACCTCTC AGACTAATGG TATGCACATA GGAGACAGCC TGAACTCCCA       200
TAAACCCTTA TCTCTGACCT GGTTAATTAC TGACTCTGAC ACAGGTATTA       250
ATATNCACAG CGCTCGAGGG GAGGCTCCTT TAGAAACCTG GTGGCCTGAT       300
CTATATGTCT GCCTCAGATC AGTCATTCCT AGTCTGACCT CAACCCCAGA       350
TATCCTCCGT GCTTACGGAT TTTATGTTTG CCCAGGACCA CCAAATAATG       400
GAAAACACTA TGGAAATCCT AGAGATTTCT TTTACAAACA ATGGAGCTGT       450
GTAACCTCTA ATGATGGAAA TCGAAAATGG CCAACCTCTC TGCAGGATAG       500
GGTAAGCTTT TCTTATGTCA ACCCCAATAA CCACCGGACC TGGAAAACGT       550
CATACAGGTA CCATTCTGGG TGTTTTCCCT CAGACCTAGA TTATCTTAAA       600
ATAAGTTTCA CCGAAAAAAA AAAACAAGAA AATATCCTAA AATGGATAAA       650
TGGTATGTCC TGGGGAATAA TATATTATAC AGGTTGGGAC AGACAACC        698
```

FIGURE 9

```
GTCATACAGG TACCATTCTG GGTGTTTTCC CTCAGACCTA GATTATCTTA      50
AAATAAGTTT CACCGAAAAA AAAAAACAAG AANATATCCT AAAATGGATA     100
AATGGTATGT CCTGGGGAAT AATATATTAT ACAGGTTGGG ACAGACAACC     150
AGGCTCCATT CTAACCATCC GACTTAAAAT AAGCCAGCTA GAGCCTCCAA     200
TGGCTATAGG CCGAATACGG TCTTAACGGG TCAAAGAACC CCAACCCCAG     250
GACCATCCTC TGATATAACT TCTAAATTAG ACCCCACTGA GTCTAACTGC     300
ACGACTAAAA CGGGNACAAA ACTTTTTAGT CTCATCCAGG GAGCTTTTC      349
```

FIGURE 10

```
AACCCCAATA ACCACCGGAC CTGGAAAACG TCATACAGGT ACCATTCTGG      50
GTGTTTTCCC TCAGACCTAG ATTATCTTAA AATAAGTTTC ACCGAAAAAA     100
AAAAACAAGA AAATATCCTA AAATGGATAA ATGGTATGTC CTGGGGAATA     150
ATATATTATA CAGGTTGGGA CAGACAACCA GGCTCCATTC TAACCATCCG     200
ACTTAAAATA AGCCAGCTAG AGCCTCCAAT GGCTATAGGA CCGAATACGG     250
TCTTAACGGG TCAAAGAACC CCAACCCAG GACCATCCTC TGATATAACT      300
TCTAAATTAG ACCCCACTGA GTCTAACAGC ACGACTAAAA CGGGGACAAA     350
ACTTTTTAGT CTCATCCAGG GAGCTTTTCA AGCTCTTAAC TCCACGACTC     400
CAGAGGCTAC CTCTTCTTGT TGGCTTTGCT TAACTTCGGG CCCACCTTAC     450
TATAAGAAAA TGGCTAAAAG AGAAAAATTC AATGTGACAA AAAAACATAG     500
AGACCAATGT ACATGGGGAT CCCAAAATAA GCTTACCCTT ACTGAGGTTT     550
CTGGAAAGGA CACCTGCATA AAAAAGGTTC CCCCATCCCA CCAACACCTT     600
TACAACCACA CTGAAGCCTT TAATCAAACC TCTGAGAGTC AATATCTGGT     650
ACCTGGTTAT GACAGGTGGT GGGCATGTAA TACTGGATTA ACCCCTTGTG     700
TTTCCACCTT GGTTTTCAAC CAAACTAAAG ACTTTTACAT TATGGTCCAA     750
ATTGTTCCCC GAGTATATTA CTATCCCAAG AAAACAATTC TCGATGAATA     800
TGATTACAGG AACCATCGAC AAAAGAAAAA ACCCATATCC CTGACACTCG     850
CAGTAATGCT CGGACTCGGA GTGATAACAG GTGTGAGAAC AGGAACTGCA     900
GCTTTAGTTA CAGGACCTCA GCAGCTAGAA ACAGGACTTA GTAACCTACA     950
TCAAATTGTA ACAGGAAATC TCCAAGCCCT AAAAAAATCT GTCAGTAACC    1000
TGGAAAAATC CCTAACCTCC TTATCTGAAG TAGTTCTACA GAATAAAAAA    1050
GGGTTAGATT TATTATTTCT AAAAAAAAGA AGATTATGTG TAGCCTTAAA    1100
GGAGAAATGC TGTTTTTATG TAGATCATTC AGGGGCCATC AGAGACTCCA    1150
TGAACAAGCT TAAAAAAAGG TTGGAGAAAC GTCGAAGGGA AAAGGAAACT    1200
TACTCAAAGA TGGTTTAAAA GATGGTTCAA CAGGTCTCCT TGGTTGGCTA    1250
CCCTACTTTC TACTTTAACA GGACCCTTAA TAGTCCTCCT CCTGTTACTC    1300
ACAGTTGGGC CATGTATTAT TAACAAGTTA ATTGCCTTCA TTAGAAAACG    1350
AATAAGTGCA GTCCAGATCA TGGTACTTAG ACAACAGTAC CAAAACCCAT    1400
CTAACAGGGA AGCTGGCCGC TAGCTCTACC AGTTCTAAGA TTAAAACTAT    1450
TAACAAGAGA AGAAGTGGGG AATGAAAGGA TAAGAAAA               1488
```

FIGURE 11

```
CACCAACGGC TGTGAAAGTC GAAAAAATCT CCACCTAGAT CCATACATCC    50
CACGTTAAGC CGGCGCCACC TCCTGATTCA GGGTGAAAAG CCAAAAAGAC   100
TAAAAATCCC CTTAAGCTTC GCCTCCATCA CATGGTTCCT TACTCTGTCA   150
ATAACCTCTC AGACTAATGG TATGCACATA GGAGACAGCC TGAACTCCCA   200
TAAACCCTTA TCTCTGACCT GGTTAATTAC TGACTCTGAC ACAGGTATTA   250
ATATCCACAG CGCTCGAGGG GAGGCTCCTT TAGAAACCTG GTGGCCTGAT   300
CTATATGTCT GCCTCAGATC AGTCATTCCT AGTCTGACCT CAACCCCAGA   350
TATCCTCCGT GCTTACGGAT TTTATGTTTG CCCAGGACCA CCAAATAATG   400
GAAAACACTA TGGAAATCCT AGAGATTTCT TTTACAAACA ATGGAGCTGT   450
GTAACCTCTA ATGATGGAAA TCGAAAATGG CCAACCTCTC TGCAGGATAG   500
GGTAAGCTTT TCTTATGTCA ACCCCAATAA CCACCGGACC TGGAAAACGT   550
CATACAGGTA CCATTCTGGG TGTTTTCCCT CAGACCTAGA TTATCTTAAA   600
ATAAGTTTCA CCGAAAAAAA AAAACAAGAA AATATCCTAA AATGGATAAA   650
TGGTATGTCC TGGGGAATAA TATATTATAC AGGTTGGGAC AGACAACCAG   700
GCTCCATTCT AACCATCCGA CTTAAAATAA GCCAGCTAGA GCCTCCAATG   750
GCTATAGGAC CGAATACGGT CTTAACGGGT CAAAGAACCC CAACCCCAGG   800
ACCATCCTCT GATATAACTT CTAAATTAGA CCCCACTGAG TCTAACAGCA   850
CGACTAAAAC GGGGACAAAA CTTTTTAGTC TCATCCAGGG AGCTTTTCAA   900
GCTCCTAACT CCACGACTCC AGAGGCTACC TCTTCTTGTT GGCTTTGCTT   950
AACTTCGGGC CCACCTTACT ATAAGAAAAT GGCTAAAAGA GAAAAATTCA  1000
ATGTGACAAA AAAACATAGA GACCAATGTA CATGGGGATC CAAAATAAG   1050
CTTACCCTTA CTGAGGTTTC TGGAAAGGAC ACCTGCATAA AAAAGGTTCC  1100
CCCATCCCAC CAACACCTTT ACAACCACAC TGAAGCCTTT AATCAAACCT  1150
CTGAGAGTCA ATATCTGGTA CCTGGTTATG ACAGGTGGTG GGCATGTAAT  1200
ACTGGATTAA CCCCTTGTGT TTCCACCTTG GTTTTCAACC AAACTAAAGA  1250
CTTTTACATT ATGGTCCAAA TTGTTCCCCG AGTATATTAC TATCCCAAGA  1300
AAACAATTCT CGATGAATAT GATTACAGGA ACCATCGACA AAAGAAAAAA  1350
CCCATATCCC TGACACTCGC AGTAATGCTC GGACTCGGAG TGATAACAGG  1400
TGTGAGAACA GGAACTGCAG CTTTAGTTAC AGGACCTCAG CAGCTAGAAA  1450
CAGGACTTAG TAACCTACAT CAAATTGTAA CAGGAAATCT CCAAGCCCTA  1500
AAAAAATCTG TCAGTAACCT GGAAAATCC CTAACCTCCT TATCTGAAGT   1550
AGTTCTACAG AATAAAAAAG GGTTAGATTT ATTATTTCTA AAAAAAAGAA  1600
GATTATGTGT AGCCTTAAAG GAGAAATGCT GTTTTTATGT AGATCATTCA  1650
GGGGCCATCA GAGACTCCAT GAACAAGCTT AAAAAAAGGT TGGAGAAACG  1700
TCGAAGGGAA AAGGAAACTT ACTCAAAGAT GGTTTAAAAG ATGGTTCAAC  1750
AGGTCTCCTT GGTTGGCTAC CCTACTTTCT ACTTTAACAG GACCCTTAAT  1800
AGTCCTCCTC CTGTTACTCA CAGTTGGGCC ATGTATTATT AACAAGTTAA  1850
TTGCCTTCAT TAGAAAACGA ATAAGTGCAG TCCAGATCAT GGTACTTAGA  1900
CAACAGTACC AAAACCCATC TAACAGGGAA GCTGGCCGCT AGCTCTACCA  1950
GTTCTAAGAT TAAAACTATT AACAAGAGAA GAAGTGGGGA ATGAAAGGAT  2000
```

FIGURE 12

```
CACCAACGGC TGTGAAAGTC GAAAAAATCT CCACCTAGAT CCATACATCC        50
CACGTTAAGC CGGCGCCACC TCCTGATTCA GGGTGAAAAG CCAAAAAGAC       100
TAAAAATCCC CTTAAGCTTC GCCTCCATCA CATGGTTCCT TACTCTGTCA       150
ATAACCTCTC AGACTAATGG TATGCACATA GGAGACAGCC TGAACTCCCA       200
TAAACCCTTA TCTCTGACCT GGTTAATTAC TGACTCTGAC ACAGGTATTA       250
ATATCCACAG CGCTCGAGGG GAGGCTCCTT TAGAAACCTG GTGGCCTGAT       300
CTATATGTCT GCCTCAGATC AGTCATTCCT AGTCTGACCT CAACCCCAGA       350
TATCCTCCGT GCTTACGGAT TTTATGTTTG CCCAGGACCA CCAAATAATG       400
GAAAACACTA TGGAAATCCT AGAGATTTCT TTTACAAACA ATGGAGCTGT       450
GTAACCTCTA ATGATGGAAA TCGAAAATGG CCAACCTCTC TGCAGGATAG       500
GGTAAGCTTT TCTTATGTCA ACCCCAATAA CCACCGGACC TGGAAAACGT       550
CATACAGGTA CCATTCTGGG TGTTTTCCCT CAGACCTAGA TTATCTTAAA       600
ATAAGTTTCA CCGAAAAAAA AAAACAAGAA AATATCCTAA AATGGATAAA       650
TGGTATGTCC TGGGGAATAA TATATTATAC AGGTTGGGAC AGACAACCAG       700
GCTCCATTCT AACCATCCGA CTTAAAATAA GCCAGCTAGA GCCTCCAATG       750
GCTATAGGAC CGAATACGGT CTTAACGGGT CAAAGAACCC CAACCCCAGG       800
ACCATCCTCT GATATAACTT CTAAATTAGA CCCCACTGAG TCTAACAGCA       850
CGACTAAAAC GGGGACAAAA CTTTTTAGTC TCATCCAGGG AGCTTTTCAA       900
GCTCCTAACT CCACGACTCC AGAGGCTACC TCTTCTTGTT GGCTTTGCTT       950
AACTTCGGGC CCACCTTACT ATAAGAAAAT GGCTAAAAGA GAAAAATTCA      1000
ATGTGACAAA AAAACATAGA GACCAATGTA CATGGGGATC CCAAAATAAG      1050
CTTACCCTTA CTGAGGTTTC TGGAAAGGAC ACCTGCATAA AAAAGGTTCC      1100
CCCATCCCAC CAACACCTTT ACAACCACAC TGAAGCCTTT AATCAAACCT      1150
CTGAGAGTCA ATATCTGGTA CCTGGTTATG ACAGGTGGTG GGCATGTAAT      1200
ACTGGATTAA CCCCTTGTGT TTCCACCTTG GTTTTCAACC AAACTAAAGA      1250
CTTTTACATT ATGGTCCAAA TTGTTCCCCG AGTATATTAC TATCCCAAGA      1300
AAACAATTCT CGATGAATAT GATTACAGGA ACCATGACA AAAGAAAAAA       1350
CCCATATCCC TGACACTCGC AGTAATGCTC GGACTCGGAG TGATAACAGG      1400
TGTGAGAACA GGAACTGCAG CTTTAGTTAC AGGACCTCAG CAGCTAGAAA      1450
CAGGACTTAG TAACCTACAT CAAATTGTAA CAGGAAATCT CCAAGCCCTA      1500
AAAAAATCTG TCAGTAACCT GGAAAAATCC CTAACCTCCT TATCTGAAGT      1550
AGTTCTACAG AATAAAAAAG GGTTAGATTT ATTATTTCTA AAAAAAAGAA      1600
GATTATGTGT AGCCTTAAAG GAGAAATGCT GTTTTTATGT AGATCATTCA      1650
GGGGCCATCA GAGACTCCAT GAACAAGCTT AAAAAAAGGT TGGAGAAACG      1700
TCGAAGGGAA AAGGAAACTT ACTCAAAGAT GGTTTAAAAG ATGGTTCAAC      1750
AGGTCTCCTT GGTTGGCTAC CCTACTTTCT ACTTTAACAG GACCCTTAAT      1800
AGTCCTCCTC CTGTTACTCA CAGTTGGGCC ATGTATTATT AACAAGTTAA      1850
TTGCCTTCAT TAGAAAACGA ATAAGTGCAG TCCAGATCAT GGTACTTAGA      1900
CAACAGTACC AAAACCCATC TAACAGGGAA GCTGGCGCT AGCTCTACCA       1950
GTTCTAAGAT TAAAACTATT AACAAGAGAA GAAGTGGGGA ATGAAAGGAT      2000
```

FIGURE 13A

```
SEQ ID NO:30        ------CAC CAACGGCTGT GAAAGTCGAA AAAATCTCCA CCTAGATCCA    43
AF038600 (5571-7600) TTGACCACAC CAACGGCTGT GAAAGTCGAA GGAATCTCCA CCTGGATCCA  5620
                                .......... .......... ..xx...... ....x.....

SEQ ID NO:30        TACATCCCAC GTTAAGCCGG CGCCACCTCC TGATTCAGGG TGAAAAGCCA    93
AF038600 (5571-7600) TGCATCCCAC GTTAAACCGG CGCCACCTCC CGATTCGGGG TGGAAAGCCG  5670
                     .x........ ....x..... .......... x...x..x.. ...x.....x

SEQ ID NO:30        AAAAGACTAA AAATCCCCTT AAGCTTCGCC TCCATCACAT GGTTCCTTAC   143
AF038600 (5571-7600) AAAAGACTGA AAATCCCCTT AAGCTTCGCC TCCATCGCGT GGTTCCTTAC  5720
                     .......x.. .......... .......... ......x.x. ..........

SEQ ID NO:30        TCTGTCAATA ACCTCTCAGA CTAATGGTAT GCACATAGGA GACAGCCTGA   193
AF038600 (5571-7600) TCTGTCAATA ACCTCTCAGA CTAATGGTAT GCGCATAGGA GACAGCCTGA  5770
                     .......... .......... .......... ..x....... ..........

SEQ ID NO:30        ACTCCCATAA ACCCTTATCT CTGACCTGGT TAATTACTGA CTCTGACACA   243
AF038600 (5571-7600) ACTCCCATAA ACCCTTATCT CTCACCTGGT TAATTACTGA CTCCGGCACA  5820
                     .......... .......... ..x....... .......... ..x.x.....

SEQ ID NO:30        GGTATTAATA TCCACAGCGC TCGAGGGGAG GCTCCTTTAG AAACCTGGTG   293
AF038600 (5571-7600) GGTATTAATA TCAACAACAC TCAAGGGGAG GCTCCTTTAG GAACCTGGTG  5870
                     ............x...x.x. ..x....... .......... .x........

SEQ ID NO:30        GCCTGATCTA TATGTCTGCC TCAGATCAGT CATTCCTAGT CTGACCTCAA   343
AF038600 (5571-7600) GCCTGATCTA TACGTTTGCC TCAGATCAGT TATTCCTAGT CTGACCTCAC  5920
                     .......... ..x..x.... .......... x......... .........x
```

FIGURE 13B

```
SEQ ID NO:30           CCCCAGATAT CCTCCGTGCT TACGGATTTT ATGTTTGCCC AGGACCACCA    393
AF038600 (5571-7600)   CCCCAGATAT CCTCCATGCT CACGGATTTT ATGTTTGCCC AGGACCACCA    5970
                       .......... .....x.... .x........ .......... ..........

SEQ ID NO:30           AATAATGGAA AACACTATGG AAATCCTAGA GATTTCTTTT ACAAACAATG    443
AF038600 (5571-7600)   AATAATGGAA AACATTGCGG AAATCCCAGA GATTTCTTTT GTAAACAATG    6020
                       .......... ....x.xx.. ......x... .......... xx........

SEQ ID NO:30           GAGCTGTGTA ACCTCTAATG ATGGAAATCG AAAATGGCCA ACCTCTCTGC    493
AF038600 (5571-7600)   GAACTGTGTA ACCTCTAATG ATGGATATTG GAAATGGCCA ACCTCTCAGC    6070
                       ..x....... .......... .....x.x.. x......... .......x..

SEQ ID NO:30           AGGATAGGGT AAGCTTTTCT TATGTCAACC CCAATA--AC CACCGGAC-C    540
AF038600 (5571-7600)   AGGATAGGGT AAGTTTTTCT TATGTCAACA CCTATACCAG CTCTGGACAA    6120
                       .......... ...x...... .........x ...x..xx.x .x.x....xx

SEQ ID NO:30           TGGAA--AAC -GTCAT--AC AGGTACC--- A-TTCTGGGT GTTTCCCTC    581
AF038600 (5571-7600)   TTTAATTACC TGACCTGGAT TAGAACTGGA AGCCCCAAGT GCTCTCCTTC    6170
                       .xx..xx.x. x.x.x.xx.x xx.x..xxxx .xxxx.xxx. .x.x...x..

SEQ ID NO:30           AGACCTAGAT TATCTTAAAA TAAGTTTCAC CGAAAAAAAA AAACAAGAAA    631
AF038600 (5571-7600)   AGACCTAGAT TACCTAAAAA TAAGTTTCAC TGAGAAAGGA AAACAAGAAA    6220
                       .......... ..x..x.... .......... x..x...xx. ..........

SEQ ID NO:30           ATATCCTAAA ATGGATAAAT GGTATGTCCT GGGGAATAAT ATATTATACA    681
AF038600 (5571-7600)   ATATCCTAAA ATGGGTAAAT GGTATGTCTT GGGGAATGGT ATATTATGGA    6270
                       .......... ....x..... ........x. .......xx. ......xx..
```

FIGURE 13C

```
SEQ ID NO:30       GGTTGGGACA GACAACCAGG CTCCATTCTA ACCATCCGAC TTAAAATAAG    731
AF038600 (5571-7600) GGCTCGGGTA AACAACCAGG CTCCATTCTA ACTATTCGCC TCAAAATAAA   6320
                   ..x.x..xx. .......... .......... ..x..x..x. .x........x

SEQ ID NO:30       CCAGCTAGAG CCTCCAATGG CTATAGGACC GAATACGGTC TTAACGGGTC    781
AF038600 (5571-7600) CCAGCTGGAG CCTCCAATGG CTATAGGACC AAATACGGTC TTGACGGGTC   6370
                   ......x... .......... .......... ..x....... ..x.......

SEQ ID NO:30       AAAGAACCCC AACCCCAGGA CCA-----T CCTCTGATAT AACTTCTAAA    825
AF038600 (5571-7600) AAAGACCCCC AACCCAAGGA CCAGGACCAT CCTCTAACAT AACTTCTGGA   6420
                   .....x.... ......x... ...xxxxxx. ......x.x. ........xx.

SEQ ID NO:30       TTAGACCCCA CTGAGTCTAA CAGCACGACT AAAACGGGGA CAAAACTTTT    875
AF038600 (5571-7600) TCAGACCCCA CTGAGTCTAG CAGCACGACT AAAATGGGGG CAAAACTTTT   6470
                   .x........ .........x .......... ....x..... x.........

SEQ ID NO:30       TAGTCTCATC CAGGGAGCTT TTCAAGCTCC TAACTCCACG ACTCCAGAGG    925
AF038600 (5571-7600) TAGCCTCATC CAGGGAGCTT TTCAAGCTCT TAACTCCACG ACTCCAGAGG   6520
                   ...x...... .......... .........x .......... ..........

SEQ ID NO:30       CTACCTCTTC TTGTTGGCTT TGCTTAACTT CGGGCCCACC TTACTATAAG    975
AF038600 (5571-7600) CTACCTCTTC TTGTTGGCTA TGCTTAGCTT CGGGCCCACC TTACTATGAA   6570
                   .......... .........x ......x... .......... ......x.x.x

SEQ ID NO:30       AAAATGGCTA AAAGAGAAAA ATTCAATGTG ACAAAAAAAC ATAGAGACCA    1025
AF038600 (5571-7600) GGAATGGCTA GAAGAGGGAA ATTCAATGTG ACAAAAGAAC ATAGAGACCA   6620
                   xx........ x.....xx.. .......... ......x... ...........
```

FIGURE 13D

```
SEQ ID NO:30     ATGTACATGG GGATCCCAAA ATAAGCTTAC CCTTACTGAG GTTTCTGGAA   1075
AF038600 (5571-7600)  ATGCACATGG GGATCCCAAA ATAAGCTTAC CCTTACTGAG GTTTCTGGAA   6670
                 ...x...... .......... .......... .......... ..........

SEQ ID NO:30     AGGACACCTG CATAAAAAAG GTTCCCCCAT CCCACCAACA CCTTTACAAC   1125
AF038600 (5571-7600)  AAGGCACCTG CATAGAAAAG GTTCCCCCAT CCCACCAACA CCTTTGTAAC   6720
                 .x.x...... ....x..... .......... .......... .....xx...

SEQ ID NO:30     CACACTGAAG CCTTTAATCA AACCTCTGAG AGTCAATATC TGGTACCTGG   1175
AF038600 (5571-7600)  CACACTGAAG CCTTTAATCA AACCTCTGAG AGTCAATATC TGGTACCTGG   6770
                 .......... .......... .......... .......... ..........

SEQ ID NO:30     TTATGACAGG TGGTGGGCAT GTAATACTGG ATTAACCCCT TGTGTTTCCA   1225
AF038600 (5571-7600)  TTATGACAGG TGGTGGGCAT GTAATACTGG ATTAACCCCT TGTGTTTCCA   6820
                 .......... .......... .......... .......... ..........

SEQ ID NO:30     CCTTGGTTTT CAACCAAACT AAAGACTTTT ACATTATGGT CCAAATTGTT   1275
AF038600 (5571-7600)  CCTTGGTTTT TAACCAAACT AAAGATTTTT GCATTATGGT CCAAATTGTT   6870
                 .........x .......... .....x...x .x........ ..........

SEQ ID NO:30     CCCCGAGTAT ATTACTATCC CAAGAAAACA ATTCTCGATG AATATGATTA   1325
AF038600 (5571-7600)  CCCCGAGTGT ATTACTATCC CGAAAAAGCA ATCCTTGATG AATATGACTA   6920
                 ........x. .......... .x.x...x.. ..x.x..... ........x.

SEQ ID NO:30     CAGGAACCAT CGACAAAAGA AAAAACCCAT ATCCCTGACA CTCGCAGTAA   1375
AF038600 (5571-7600)  CAGAAATCAT CGACAAAAGA GAGAACCCAT ATCCTCTGACA CTTGCTGTGA   6970
                 ...x.x.... .......... x.x....... .....x.... ..x..x..x.
```

FIGURE 13E

```
SEQ ID NO:30           TGCTCGGACT CGGAGTGATA ACAGGTGTGA GAACAGGAAC TGCAGCTTTA   1425
AF038600 (5571-7600)   TGCTCGGACT TGGAGTGGCA GCAGGTGTAG GAACAGGAAC AGCTGCCCTG   7020
                       .......... .......x.. ......xx.. x.........x..x..xx.x

SEQ ID NO:30           GTTACAGGAC CTCAGCAGCT AGAAACAGGA CTTAGTAACC TACATCAAAT   1475
AF038600 (5571-7600)   GTCACGGGAC CACAGCAGCT AGAAACAGGA CTTAGTAACC TACATCGAAT   7070
                       ..x.x..... .x........ .......... .......... ......x...

SEQ ID NO:30           TGTAACAGGA AATCTCCAAG CCCTAAAAAA ATCTGTCAGT AACCTGGAAA   1525
AF038600 (5571-7600)   TGTAACAGAA GATCTCCAAG CCCTAGAAAA ATCTGTCAGT AACCTGGAGG   7120
                       ........x. .x........ .....x.... .......... ........xx

SEQ ID NO:30           AATCCCTAAC CTCCTTATCT GAAGTAGTTC TACAGAATAA AAAAGGGTTA   1575
AF038600 (5571-7600)   AATCCCTAAC CTCCTTATCT GAAGTAGTCC TACAGAATAG AAGAGGGTTA   7170
                       .......... .......... ........x. .........x .x........

SEQ ID NO:30           GATTTATTAT TTCTAAAAAA AAGAAGATTA TGTGTAGCCT TAAAGGAGAA   1625
AF038600 (5571-7600)   GATTTATTAT TTCTAAAAGA AGGAGGATTA TGTGTAGCCT TGAAGGAGAA   7220
                       .......... ........x. .x..x..... .......... .x........x.

SEQ ID NO:30           ATGCTGTTTT TATGTAGATC ATTCAGGGGC AAACGTCGAA TCCATGAACA   1675
AF038600 (5571-7600)   ATGCTGTTTT TATGTGGATC ATTCAGGGGC AAGCGTCGAA TCCATGAACA   7270
                       .......... .....x.... .......... ..x....... ..........

SEQ ID NO:30           AGCTTAAAAA AAGGTTGGAG AAACGTCGAA GGGAAAAGGA AACTTACTCA   1725
AF038600 (5571-7600)   AGCTTAGAGA AAGGTTGGAG AAGCGTCGAA GGGAAAAGGA AACT-ACTCA   7319
                       ......x.x. .......... ..x....... .......... ....-.....
```

FIGURE 13F

```
SEQ ID NO:30            AAGATGGTTT AAAAGATGGT TCAACAGGTC TCCTTGGTTG GCTACCCTAC  1775
AF038600 (5571-7600)    AGGGTGGTTT GAGGGATGGT TCAACAGGTC TCTTTGGTTG GCTACCCTAC  7369
                        .x.x...... x.xx...... .......... ..x....... ..........

SEQ ID NO:30            TTTCTACTTT AACAGGACCC TTAATAGTCC TCCTCCTGTT ACTCACAGTT  1825
AF038600 (5571-7600)    TTTCTGCTTT AACAGGACCC TTAATAGTCC TCCTCCTGTT ACTCACAGTT  7419
                        .....x.... .......... .......... .......... ..........

SEQ ID NO:30            GGGCCATGTA TTATTAACAA GTTAATTGCC TTCATTAGAA AACGAATAAG  1875
AF038600 (5571-7600)    GGGCCATGTA TTATTAACAA GTTAATTGCC TTCATTAGAG AACGAATAAG  7469
                        .......... .......... .......... .........x ..........

SEQ ID NO:30            TGCAGTCCAG ATCATGGTAC TTAGACAACA CCATCTAACA GTACCAAAAC  1925
AF038600 (5571-7600)    TGCAGTCCAG ATCATGGTAC TTAGACAACA CCGTCTAGCA GTACCAAAGC  7519
                        .......... .......... .......... ..x....x.. .......x..

SEQ ID NO:30            GGGAAGCTGG CCGCTAGCTC TACCAGTTCT AAGATTAAAA CTATTAACAA  1975
AF038600 (5571-7600)    GGGAAGCTGG CCGCTAGCTC TACCAGTTCT AAGATTAGAA CTATTAACAA  7569
                        .......... .......... .......... .......x.. ..........

SEQ ID NO:30            GAGAAGAAGT GGGGAATGAA AGGAT----- -                    2000
AF038600 (5571-7600)    GAGAAGAAGT GGGGAATGAA AGGATGAAAA T                    7600
                        .......... .......... .....
```

MOLECULAR SEQUENCE OF SWINE RETROVIRUS AND METHODS OF USE

This application claims the benefit of U.S. Provisional Patent Application No. 60/097,015, filed Aug. 18, 1998, and contains additional matter.

FIELD OF THE INVENTION

This invention relates to newly identified polynucleotides, polypeptides encoded by such polynucleotides, the use of such polynucleotides and polypeptides, as well as the production of such polynucleotides and polypeptides. More particularly, the polypeptides of the present invention are porcine endogenous retrovirus (PERV) polypeptides. The invention also relates to methods of using the PERV polypeptides and polynucleotides encoding the PERV polypeptides.

BACKGROUND OF THE INVENTION

Organ procurement currently poses one of the major problems in organ transplantation, as the number of patients requiring transplants far exceeds the number of organs available. A path for eliminating the shortage of donor organs is to develop the technologies required to transplant nonhuman organs into humans, i.e., xenotransplantation.

Potential sources of xenogeneic organs include nonhuman primates and pigs. There are serious problems with considering nonhuman primates as donors. Chimpanzees, the closest nonhuman primates phylogenetically, are far too rare to be considered. Baboons are too small to be an appropriate donor for most organ transplants. Even the largest baboons weigh less than 40 kg. In addition, the gestation times and productivity of primates would not allow a commercially significant generation of source animals.

The physiology of many organ systems of pigs has been shown to be highly similar to the human counterparts (Sachs, D. H. 1994. Veterinary Immunology & Immunopathology, 43:185–191). Pigs come in many different sizes including the breed described as miniature porcine. The miniature swine have a variety of advantages as potential xenograft donors. They achieve adult weights of approximately 100–150 kg, a size which is more compatible to human weights than the domestic pig which reaches weights of over 500 kg. Through a selective breeding program over the past 20 years partially inbred, miniature swine have been produced (Sachs et al. 1976. Transplantation 22: 559–567; Sachs, 1992. In Swine as models in biomedical research. M. Swindle, D. Moody, and L. Phillips, eds. (Ames Iowa State Univ. Press) pp 3–15 ; Sachs, 1994. veterinary Immunology & Immunopathology, 43: 185–191).

These breeding program has resulted in herds of animals that are genetically well characterized. These animals have been used in large animal model studies for many years and have, like their domestic counterparts, very favorable breeding characteristics for the production of donor animals.

A central concern regarding xenotransplantation is the risk of xenosis, infection by organisms transferred with the xenograft into both the transplant recipient and the general population. The risk of viral infection is increased in transplant recipients by the presence of factors commonly associated with viral activation, e.g., immune suppression, graft-versus-host disease, graft rejection, viral co-infection, and cytotoxic therapies. Type C retroviruses from cells of swine origin have been characterized (Arida, E. and Hultin, T. 1977. Am. J. Public Health 67: 380; Armstrong et al. 1971. J. Gen. Virol. 10: 195–198; Benveniste, R. E. and Todaro, G. J. 1973. Proc. Natl. Acad. Sci. USA 70:3316–3320; Bouillant et al. 1975. J. Gen. Virol. 27: 173–180; Frazier, M. E. 1985. Arch. Virol. 83: 83–97; Lieber et al. 1975. Virology 66:616–619; Suzuka et al. 1985. FEBS Lett. 183: 124–128; Suzuka et al. 1986. FEBS Lett. 198: 339–343; Todaro et al. 1974. Virology 58: 65–74; Woods et al. 1973. J. Virol. 12: 1184–1186; Akiyoshi et al. 1988 J. Virol. 72: 4503–4507); as yet, no disease following infection by these viruses has been identified. A recent report demonstrated that a virus from the PK15 (porcine kidney-derived) cells can infect human cells in vitro (Patience et al., 1997. Nature Medicine 3:276–282).

Characterization of swine cells and cell lines has resulted in the identification of at least three pig endogenous retrovirus sequences (PERV-A, -B, -C), (WO 97/40167; WO 97/21836; Le Tissier, et al. 1997. Nature 389: 681–682; Czauderna, F. et al. 1998: Genbank Accession Number Y17013). These sequences have distinct envelope (env) genes but share highly conserved sequences in the rest of the genome. Southern blot analysis of pig tissues and cell lines (Patience et al., 1997. Nature Medicine 3:276–282) showed the presence of numerous loci in DNA extracted from normal pig hearts and from pig cell lines. The banding profile for normal pig hearts is similar to that of the pig cell lines and is typical of an endogenous inherited retrovirus suggesting heterogeneity with approximately 50 integration sites. These results were confirmed and extended to analysis of MHC-inbred miniature swine where the numbers of potentially full-length provirus copies are approximately 8 to 15 per genome for inbred and outbred swine and 10 to 20 in PK15 cells (Akiyoshi et al. 1998. J. Virology, 72:4503–4507).

The env gene product determines host range and cell tropism. Host range analyses using retrovirus vectors bearing corresponding env proteins showed that PERV-A and PERV-B envs have wider host range including several human cell lines compared to PERV-C env which infected only 2 pig cell lines and 1 human cell line. All three classes of PERVs have been shown to infect pig cells. Receptors for PERV-A and PERV-B have been shown to be present on cells of some other species, including mink, rat, mouse and dog. Interference studies showed that the three PERV strains use distinct receptors to each other and to a number of other type C mammalian retroviruses.

SUMMARY OF THE INVENTION

It is an object of the present invention to provide a method for the detection of known PERV sequences or new PERV sequences.

A further object of the present invention is to provide a polynucleotide sequence and polypeptide which it encodes that correspond to a new PERV env sequence, which may be called PERV-D. The new sequence is found in the PK15 cell line, for example.

A still further object of the present invention is to provide at least one set of primers suitable for conducting a polymerase chain reaction, wherein at least one of the two primers has a polynucleotide sequence that is of low sequence identity to PERV-A and PERV-B env regions but is capable of hybridizing to known or unknown PERV sequences in the PERV-C env sequence. Even when the env sequences are shown as the positive strand, probes or primers may be directed to either strand where integrated or cDNA retroviral sequences are to be detected.

A yet further object of the present invention is to provide a method for detecting retroviruses in a sample of porcine or human tissues, as well as probes and primers that may be utilized in such a method. The porcine or human tissues may include primary porcine tissue and human cell lines which have been cultivated in the presence of a porcine cell line, or human tissues which are from a human or nonhuman primate who has received a xenotransplant. Nucleic acid (e.g., MRNA, total RNA, DNA or total nucleic acid) from the tissues or cells may be probed directly or, if desired, retroviral sequences may be amplified using primers suitable for amplifying retroviral sequences in general prior to detecting PERV env sequences of the invention.

A still further object of the invention is to provide a vaccine against novel PERV polypeptides of the invention which could be used to protect a xenotransplant recipient from productive proliferation of PERV.

An even further object of the present invention is to provide antibodies that are capable of binding to an epitope on such PERV polypeptides. Such antibodies can be used for diagnosis of the presence of PERV polypeptides or used as part of a passive immunity therapeutic treatment method.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIG. 1 shows a PERV-D sequence (SEQ ID. NO:1) that encodes a PERV-D polypeptide of the present invention. The gene portion shown in FIG. 1 encodes a portion of the PERV-D env polypeptide. Sequencing was performed using the SequiThermEXCEL™ II DNA sequencing kit (Epicentre Technologies, Inc., Madison, Wis.).

FIG. 2 shows the deduced polypeptide sequence (SEQ ID. NO: 2) of the PERV-D DNA sequence (SEQ ID. NO: 1) shown in FIG. 1. The amino acids of the sequence are represented by standard one-letter codes.

FIG. 3 is an illustration of amino acid sequence identity between a portion of the PERV-D env polypeptide of FIG. 2 (row 1 of the compared sequences) and four other PERV env polypeptides (POEV is row 2 of the compared sequences (SEQ ID NO: 3) taken from WO 97/40167, FIG. 3; PERV-B (SEQ IND NO:4) is row 3 of the compared sequences, taken from Genbank Accession Number Y12239; PERV-A is row 4 (SEQ ID NO: 5) of the compared sequences, taken from Genbank Accession Number Y12238; and PERV-C is row 5 (SEQ ID NO: 6), of the compared sequences, taken from Genbank Accession Number AF038600). Standard one-letter abbreviations for amino acids are used and dashes are utilized to indicate indiviudal gap spaces (each corresponding to an individual amino acid residue that is present in at least one other sequence) that are required to align the sequences.

FIG. 4A is a comparison of the nucleic acid sequence of a portion of the PERV-D env gene (SEQ ID NO:1) with the nucleic acid sequence of a portion of the PERV-A env gene (SEQ ID NO:7) that corresponds to nucleotides 364–809 of GenBank Accession Number Y12238. Dashes are utilized in each of the aligned sequences to indicate individual gap spaces (each corresponding to an individual nucleotide that is present in the other sequence) that are required to align the sequences.

FIG. 4B corresponds to the alignment of FIG. 4A, except that only the aligned nucleotides that are different (mismatched) are shown. Dashes indicate individual gap spaces introduced to provide an alignment and correspond to an individual nucleotide present in the other sequence. Dots indicate the nucleotide positions having identical nucleotides. Due to the large number of gaps required for alignment, the identity between the two sequences is not very high.

FIG. 5A is a comparison of the nucleic acid sequence of a portion of the PERV-D env gene (SEQ ID NO:1) with the nucleic acid sequence of a portion of the PERV-B env gene (SEQ ID NO:8) that corresponds to nucleotides 1350–1623 of GenBank Accession Number Y12239. Dashes are utilized in each of the aligned sequences to indicate individual gap spaces (each corresponding to an individual nucleotide that is present in the other sequence) that are required to align the sequences.

FIG. 5B corresponds to the alignment of FIG. 5A, except that only the aligned nucleotides that are different (mismatched) are shown. Dashes indicate individual gap spaces introduced to provide an alignment and correspond to an individual nucleotide present in the other sequence. Dots indicate the nucleotide positions having identical nucleotides. Very few alignment gaps are present but the number of mismatched nucleotides is substantial. Therefore, the identity between the two sequences is low.

FIG. 6A is a comparison of the nucleic acid sequence of a portion of the PERV-D env gene (SEQ ID NO:1) with the nucleic acid sequence of a portion of the PERV-C env gene (SEQ ID NO:9) that corresponds to nucleotides 6075–6331 of GenBank Accession Number AF 038600. Dashes are utilized in each of the aligned sequences to indicate individual gap spaces (each corresponding to an individual nucleotide that is present in the other sequence) that are required to align the sequences. The overall sequence identity is about 79%.

FIG. 6B corresponds to the alignment of FIG. 6A, except that only the aligned nucleotides that are different (mismatched) are shown. Dashes indicate individual gap spaces introduced to provide an alignment and correspond to an individual nucleotide present in the other sequence. Dots indicate the nucleotide positions having identical nucleotides. Very few alignment gaps are present and the number of mismatched nucleotides is not very high. Therefore, the identity between these two polynucleotide sequences portions is quite high, being about 79% overall identity over the compared sequence stretches.

FIG. 7A is a comparison of the nucleic acid sequence of a portion of the PERV-D env gene (SEQ ID NO:1) with the nucleic acid sequence of a portion of the POEV env gene (SEQ ID NO:10) that corresponds to WO 97/40167 (FIG. 3 nucleotides 6057–6333). Dashes are utilized in each of the aligned sequences to indicate individual gap spaces (each corresponding to an individual nucleotide that is present in the other sequence) that are required to align the sequences.

FIG. 7B corresponds to the alignment of FIG. 7A; except that only the aligned nucleotides that are different (mismatched) are shown. Dashes indicate individual gap spaces introduced to provide an alignment and correspond to an individual nucleotide present in the other sequence. Dots indicate the nucleotide positions having identical nucleotides. Very few alignment gaps are present but the number of mismatched nucleotides is somewhat substantial. Therefore, the identity between the two sequences is not very high.

FIG. 8 shows the nucleotide sequence of the 5' env fragment of PERV-D (SEQ ID NO: 18).

FIG. 9 shows the nucleotide sequence determined by extending the sequence analysis into the proline-rich region of the PERV-D env region (SEQ ID NO: 22).

FIG. 10 shows the nucleotide sequence as determined for the 3'-end of the PERV-D env region (SEQ ID NO: 24).

FIG. 11 shows the contiguous sequence that was compiled from SEQ ID NOS: 18, 22, and 24 to generate SEQ ID NO: 25.

FIG. 12 shows the sequence of a 2 kb fragment containing the PERV-D env region (SEQ ID NO: 30).

FIG. 13 shows a comparison of the nucleotide sequences of PERV-D and PERV-C (AF038600) env regions. The sequences were aligned using the Geneworks® software. Gaps are indicated by dashes and differences are indicated by the "X" on the line below the sequences. FIGS. 13A through 13F follow in sequence and each is a continuation of the previous.

DETAILED DESCRIPTION OF THE INVENTION

Figure 14:
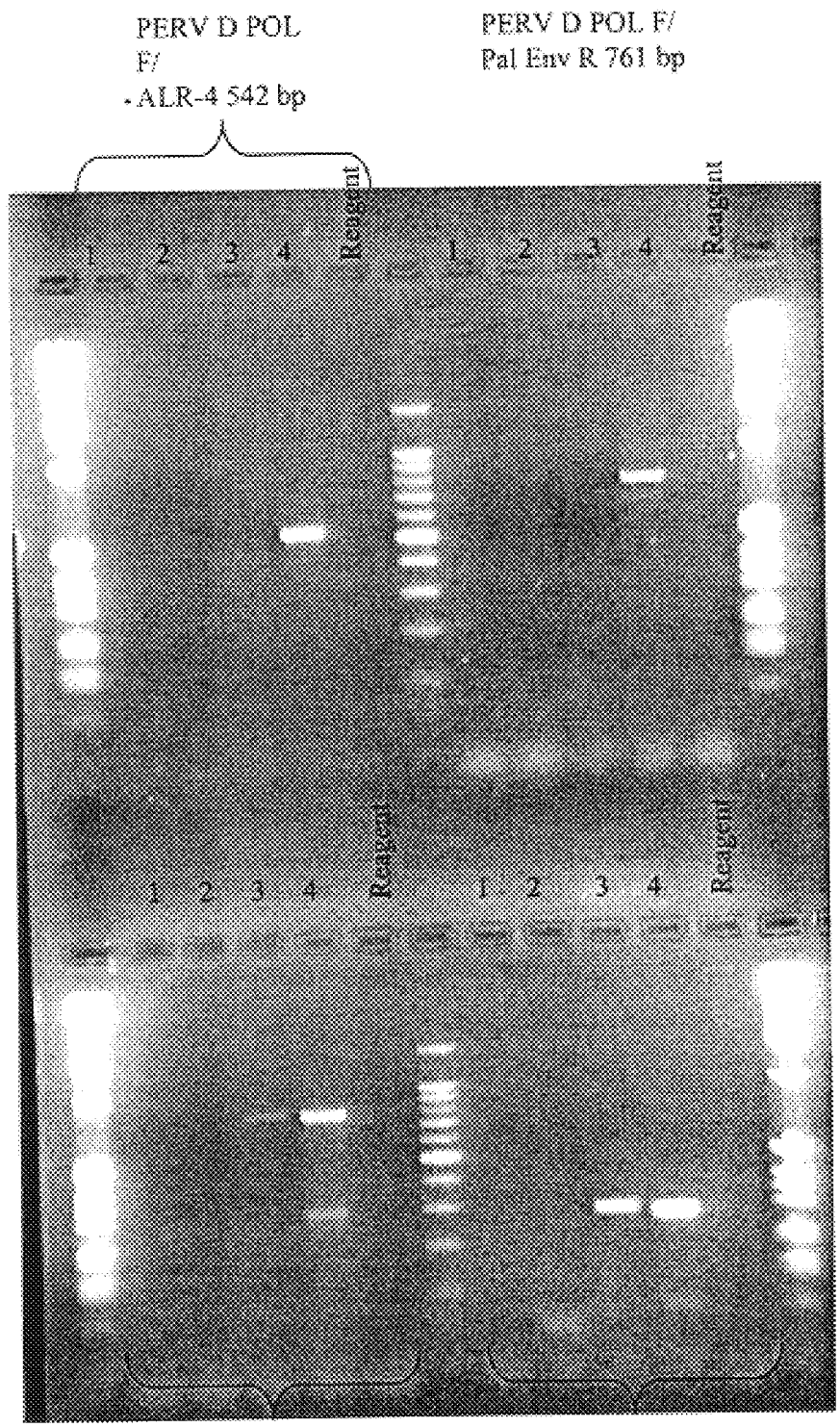
FIG. 14 shows a photograph of an agarose gel on which PCR (polymerase chain reaction) products of the assay, designed to specifically detect PERV-D sequences, were electrophoresed. Lane 1: PERV A DNA (2A2.A cells), Lane 2: PERV B DNA (2A2.B cells, Lane 3: Neptune 6 DNA dil 3A (1000 copies/5 μl), Lane 4: PK15 DNA; Reagent: assay run in the presence of no added template DNA.

In accordance with an aspect of the present invention, there are provided isolated nucleic acids (polynucleotides) which encode the mature polypeptides comprising the amino acid sequence of SEQ ID NO:2. The mature forms of the PERV-D polypeptide with and without an N-terminal methionine group which comprise the amino acid sequence of SEQ ID NO:2 are contemplated.

Polynucleotides encoding the polypeptide of the present invention have been isolated from the porcine cell line PK-15 (ATCC number CCL-33). Primer sequences were utilized that would not be expected to hybridize to PERV-A or PERV-B. The polynucleotide contains an open reading frame encoding the polypeptide as shown in FIG. 2, which is a portion of the PERV-D env polypeptide. The PERV-D polypeptide portion exhibits a high degree of homology at the amino acid level to a portion of PERV-C (encoded by nucleotides 6057–6331 of GenBank Accession Number AF 038600) such that the underlying polynucleotide sequences that encode the two polypeptides have about 79% identity (see FIG. 6A). The corresponding polypeptide sequence for the invention polypeptide (SEQ ID NO:2) is set forth as part of SEQ ID NO:6 (amino acids 147–241).

In accordance with a further aspect of the present invention the nucleic acid sequence according to SEQ ID NO:1 or an appropriate fragment thereof may be utilized under stringent hybridization conditions to isolate from the PK15 cell line (or other tissue source) by procedures known in the art, the DNA encoding the mature PERV-D env polypeptide. Likewise the polypeptide having an amino acid sequence according to SEQ ID NO:2, or an immunogenic fragment thereof, may be utilized to produce antibodies specific for the polypeptide according to SEQ ID NO:2 (or a fragment thereof), for the mature PERV-D env polypeptide, or for polypeptides such as the PERV-C env polypeptide. Such antibodies are in turn useful to detect the presence of such polypeptides when they are expressed by a clone or a transformed host cell to indicate the presence of the respective polynucleotides encoding such polypeptides.

The polynucleotides of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the polypeptides may comprise an amino acid sequence identical to the coding sequence shown in FIG. 1 (SEQ ID NO:1) or may be a different coding sequence which coding sequence, as a result of the redundancy or degeneracy of the genetic code, encodes the polypeptide of SEQ. ID NO:2, the coding sequence DNA polynucleotide for which is shown in FIG. 1 (SEQ ID NO:1).

The polynucleotides which encode a mature polypeptide of the present invention comprise the polynucleotide sequence encoding the polypeptide of SEQ ID NO:2 and may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptides.

Thus, the term "polynucleotide encoding a polypeptide" encompasses a polynucleotide which includes coding sequence for the polypeptide and may also include additional coding and/or non-coding sequence such as introns.

The present invention further relates to variants of the hereinabove described polynucleotides which encode fragments, analogs and derivatives of the mature polypeptide comprising amino acid sequence shown in SEQ ID NO:2. The variant of the polynucleotides may be a naturally occurring allelic variant of the polynucleotides or a non-naturally occurring variant of the polynucleotides.

Further particularly preferred in this regard are polynucleotides encoding the PERV-D env polypeptide variants, analogs, derivatives and fragments, and variants, analogs and derivatives of the fragments, which comprise the amino acid sequence of the polypeptide of SEQ ID NO:2 in which several, a few, 5 to 10, 1 to 5, 1 to 3, 2, 1 or no amino acid residues are substituted, deleted or added, in any combination. Especially preferred among these are conservative substitutions, additions and deletions, which do not alter the properties and activities of the PERV-D env polypeptide, Also especially preferred in this regard are conservative substitutions. Most highly preferred are mature polypeptides comprising the amino acid sequence set forth in SEQ ID NO:2 without substitutions.

Thus, the present invention includes polynucleotides encoding polypeptides comprising the polypeptide as set forth in SEQ ID NO:2 as well as variants of such polynucleotides which variants encode a fragment, derivative or analog of the polypeptides set forth in SEQ ID NO:2. Such nucleotide variants include deletion variants, substitution variants and addition or insertion variants.

As hereinabove indicated, the polynucleotides may have a coding sequence which is a naturally occurring allelic variant of the coding sequences comprising the coding portion of the polynucleotide sequence shown in FIG. 1 (of SEQ ID No:1). As known in the art, an allelic variant is an alternate form of a polynucleotide sequence which may have a substitution, deletion or addition of one or more nucleotides, which does not substantially alter the function of the encoded polypeptide.

The present invention also includes polynucleotides which may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotides of the present invention may encode a mature protein, a protein having a prosequence or a protein having both a prosequence and a presequence (leader sequence).

The polynucleotides of the present invention may also have the coding sequence fused in frame to a marker sequence which allows for purification of the polypeptides of the present invention. The marker sequence may be a hexa-histidine tag supplied by a pQE-9 vector to provide for purification of the mature polypeptides fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the polynucleotide sequences of the present invention may be used as a hybridization probes for a cDNA or DNA library to isolate the full length gene and to isolate other genes which have a high sequence similarity to the gene or similar biological activity. Probes of this type preferably have at least 30 bases and may contain, for example, 50 or more bases. The probe may also be used to identify a cDNA clone or DNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of porcine DNA, genomic DNA or mRNA to determine which members of the library the probe hybridizes to.

The present invention further relates to polynucleotides which hybridize to the hereinabove-described polynucleotide sequences if there is at least 85%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide comprising the amino acid sequence encoded by the DNA of FIG. 1 (comprising SEQ ID NO:2).

Alternatively, the polynucleotide may have at least 30 bases, preferably at least 50 bases, and more preferably at least 75 bases which hybridize to a polynucleotide of the present invention and which has an identity thereto, as hereinabove described, and which may or may not retain activity. For example, such polynucleotides may be employed as probes for the gene comprising the polynucleotide of SEQ ID NO:1, for example, for recovery of the polynucleotide or as a diagnostic probe or as a PCR primer.

Thus, the present invention is directed to a polynucleotide comprising a polynucleotide having at least 85% identity, preferably at least 90% and more preferably at least a 95% identity to a polynucleotide of FIG. 1 or to a polynucleotide which encodes the polypeptide of FIG. 2 and polynucleotides complementary thereof, which portions have at least 30 consecutive, preferably at least 50 consecutive bases and may have at least 75 consecutive bases and to polypeptides encoded by such polynucleotides. Preferred polynucleotide fragments are fragments that contain all or a portion of SEQ ID NO:1, with such fragments generally containing at least 30 consecutive bases of SEQ ID NO:1.

The present invention further relates to mature PERV-D envelope protein that includes a polypeptide which has the deduced amino acid sequence as set forth in SEQ ID NO:2, as well as fragments, analogs and derivatives of such polypeptide.

The terms "derivative" and "analog" when referring to the mature polypeptides comprising the polypeptide as set forth in SEQ ID NO:2, means polypeptides which retain essentially the same biological function or activity as such polypeptides. Thus, an analog includes a proprotein which can be activated by cleavage of the proprotein portion to produce an active mature polypeptide.

Among the particularly preferred embodiments of the invention are mature polypeptides comprising the amino acid sequence as set forth in SEQ ID NO:2, variants, analogs, derivatives and fragments thereof, and variants, analogs and derivatives of the fragments. Alternatively, particularly preferred embodiments of the invention in this regard are PERV-D env polypeptides, variants, analogs, derivatives and fragments thereof, and variants, analogs and derivatives of the fragments.

Further particularly preferred are variants, analogs, derivatives and fragments of the PERV-D env polypeptide (and variants, analogs and derivatives of the fragments), comprising the amino acid sequence of the polypeptide as set forth in SEQ ID NO:2 or of the DNA in the clone, in which several, a few, 5 to 10, 1 to 5, 1 to 3, 2, 1 or no amino acid residues are substituted, deleted or added, in any combination. Especially preferred among these are conservative substitutions, additions and deletions, which do not alter their properties and activities as compared to those of the PERV-D env polypeptide. Most highly preferred are mature polypeptides comprising the amino acid sequence as set forth in SEQ ID NO:2, or of the deposited clone, without substitutions.

The polypeptides of the present invention may be recombinant polypeptides, natural polypeptides or synthetic polypeptides, preferably recombinant polypeptides.

The fragment, derivative or analog of the polypeptides comprising the amino acid sequence set forth in SEQ ID NO:2 may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include polypeptides comprising the polypeptide of SEQ ID NO:2 (in particular the PERV-D env polypeptide) or a fragment thereof, which fragment may be all or a portion of the polypeptide of SEQ ID NO:2, as well as polypeptides which have at least 85% similarity (preferably at least 85% identity) to such polypeptides, and which have at least 90% similarity (more preferably at least 90% identity) to such polypeptides and still more preferably at least 95% similarity (still more preferably at least 95% identity) to such polypeptides comprising the amino acid sequence of SEQ ID NO:2 and also include portions of such polypeptides with such portion of the polypeptide generally containing at least 30 amino acids, more generally at least 40 amino acids and may comprise at least 50 amino acids. Preferred are fragments comprising 30 or more consecutive amino acids, more preferred are fragments with at least 40 amino acids and even more preferred are fragments comprising 50 or more amino acids of the polypeptide of SEQ ID NO:2.

As known in the art "similarity" between two polypeptides is determined by comparing the amino acid sequence and its conserved amino acid substitutes of one polypeptide to the sequence of a second polypeptide. For such a determination, two amino acid sequences are compared along a stretch of their sequences, any gap (or gaps) introduced in one sequence to improve the alignment and similarity to the other sequences is counted as spaces of dissimilarity equal to the number of amino acids corresponding to the gap which are present in the second sequence, and the total number of similar amino acids are divided by the total number of amino acids present in the comparison area which counts the spaces of gaps as part of the comparsion area.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the $E.$ $coli.$ lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.$ $coli.$ The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as $E.$ $coli$, Streptomyces, *Salmonella typhimurium*; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pBluescript SK, pBSKS, pNH8A, pNH16a, pNH18A, pNH46A (Stratagene); pTRC99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene products encoded by the recombinant sequences. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa, 293 and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The polynucleotides and polypeptides of the present invention may be employed as research reagents and materials for discovery of treatments and diagnostics for human disease. For example, the polynucleotides and polypeptides encoded by such polynucleotides may also be utilized for in vitro purposes related to scientific research, synthesis of DNA and manufacture of DNA vectors and for designing therapeutics and diagnostics for human disease.

The invention also provides a method for identifying retroviruses in a sample of porcine tissue or of human or non-human primate tissue by contacting a mixture of polynucleotides from a cell sample with a polynucleotide unique to the retroviruses (or unique to a class of retroviruses) such as a porcine retrovirus comprising a PERV-D polynucleotide sequence and identifying any polynucleotide that has hybridized with the polynucleotide unique to PERV-D (or unique to either or both of PERV-C and PERV-D, or the like). In a preferred embodiment, the hybridization polynucleotide utilized to probe the polynucleotides of the tissue sample is bound to a solid support. Thus, for example, the identification of the above PERV-D sequence portion enables such nucleic acid sequence or portion thereof to be utilized as a diagnostic reagent to identify porcine retroviruses, such as by using gene expression array technology. Labeled (e.g. fluorescent or radiolabeled) mixtures of total cellular mRNA, RNA or genomic DNA hybridize to cognate elements of the PERV-D polynucleotide on a chip based array and allow for the accurate detection of genes specific to the porcine retrovirus. This technology is described, for example, in Schena, *Bioessays*, 18 (5):427–431 (May 1996) and O'Donnell-Maloney & Little, *Genet. Anal.*, 13 (6):151–157 (Dec. 1996).

The polypeptides of the present invention and fragments and analogs and derivatives thereof may be utilized to produce antibodies that may be utilized to identify porcine retrovirus presence in tissue, as well as their proliferation or other activity. Further, the probes which are fragments of the polynucleotide according to SEQ ID NO:1 (or of its variants or derivatives), or complements thereof, as described above may be utilized to identify procine retrovirus presence in tissue, as well as their proliferation or other activity. Such probes may be utilized in hybridization assays to detect the retrovirus that have the gene for PERV-D, for example.

Individuals carrying retroviruses with sequences such as the PERV-D env polypeptide gene may be detected at the DNA level by a variety of techniques. Nucleic acids for diagnosis may be obtained from a patient's cells, such as from blood, urine, saliva, tissue biopsy and autopsy material. The genomic or cellular DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding the PERV-D (or to portions of both PERV-D and PERV-C) polypeptide can be used to identify and analyze for porcine retroviruses in the tissue. Even related retrovirus sequences can be identified. For example, deletions and insertions can be detected by a change in size of the amplified product in comparison to the normal genotype. Point mutations can be identified by hybridizing amplified DNA to radiolabeled PERV-D env polypeptide RNA or alternatively, radiolabeled PERV-D env polypeptide antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, retroviruses have nucleotide sequence differences or mutations can also be detected by in situ analysis.

The present invention also relates to a diagnostic assay for detecting expression of the PERV-D env polypeptide in various tissues. Assays used to detect levels of the PERV-D env polypeptide in a sample derived from a host are well-known to those of skill in the art and include radioimmunoassays, competitive-binding assays, Western Blot analysis, ELISA assays and "sandwich" assay. An ELISA assay (Coligan, et al., Current Protocols in Immunology, 1 (2), Chapter 6, (1991)) initially comprises preparing an antibody specific to the PERV-D (or specific to PERV-C and PERV-D polypeptides, or the like, as a class) env polypeptide antigen, preferably a monoclonal antibody. In addition a reporter antibody is prepared against the monoclonal antibody. To the reporter antibody is attached a detectable reagent such as radioactivity, fluorescence or, in this example, a horseradish peroxidase enzyme. A sample is removed from a host and incubated on a solid support, e.g. a polystyrene dish, that binds the proteins in the sample. Any free protein binding sites on the dish are then covered by incubating with a non-specific protein like BSA. Next, the monoclonal antibody is incubated in the dish during which time the monoclonal antibodies attach to any PERV-D (or to either of PERV-C and PERV-D) polypeptide attached to the polystyrene dish. All unbound monoclonal antibody is washed out with buffer. The reporter antibody linked to horseradish peroxidase is now placed in the dish resulting in binding of the reporter antibody to any monoclonal antibody bound to the PERV-D polypeptide. Unattached reporter antibody is then washed out. Peroxidase substrates are then added to the dish and the amount of color developed in a given time period is a measurement of the amount of the PERV-D polypeptide present in a given volume of patient sample when compared against a standard curve.

A competition assay may be employed wherein antibodies specific to the PERV-D polypeptide are attached to a solid support, labeled PERV-D polypeptide and a sample derived from the host are passed over the solid support, and the amount of label detected. The label can be detected, for example, by liquid scintillation chromatography and can be correlated to a quantity of the PERV-D polypeptide present in the sample.

A "sandwich" assay is similar to an ELISA assay. In a "sandwich" assay the PERV-D polypeptide is passed over a solid support and binds to antibody attached to a solid support. A second antibody is then bound to the PERV-D polypeptide. A third antibody which is labeled and specific to the second antibody is then passed over the solid support and binds to the second antibody and an amount can then be quantified.

Antibodies against the PERV-D polypeptides may be employed for the treatment of individuals infected by porcine retroviruses to provide passive immunity by combining the antibodies with a suitable pharmaceutical carrier. Such compositions comprise a therapeutically effective amount of the antibodies, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the antibodies against the PERV-D polypeptides may be employed in conjunction with other therapeutic compounds.

The pharmaceutical compositions may be administered in a convenient manner such as by the topical, intravenous, intraperitoneal, intramuscular, intratumor, subcutaneous, intranasal or intradermal routes. The pharmaceutical compositions are administered in an amount which is effective for treating and/or prophylaxis of the specific indication. In general, the antibodies against the polypeptides will be administered in an amount of at least about 10 $\mu$g/kg body weight and in most cases they will be administered in an amount not in excess of about 8 mg/Kg body weight per day. In most cases, the dosage is from about 10 $\mu$g/kg to about 1 mg/kg body weight daily, taking into account the routes of administration, symptoms, etc.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

Antibodies specific to the polypeptide of the present invention may be employed as a diagnostic to determine the presence of a retrovirus in tissue, which retrovirus expresses the PERV-D polypeptide (or a related polypeptide) in a sample derived from a host by techniques known in the art. Such antibodies may be useful to provide passive immunity in a host.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

Such antibodies to the polypeptides of the present invention may be utilized to detect the presence or the absence of the polypeptides of the present invention. Thus, they are useful in an assay to verify the successful insertion of the polynucleotides of the present invention (as part of a construct) into a host cell. Thus, the protein encoded by the inserted polynucleotide according to the present invention, when expressed by the transformed host cell, serves as a "marker" for the successful insertion of the polynucleotide that can be detected by an antibody for the marker.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic is oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 μg of approximately equimolar amounts of the DNA fragments to be ligated.

"Identity" means, as utilized in the context of the present specification and claims, a comparison with respect to the degree of sameness between a first sequence and a second sequence (the first sequence may also be referred to as the "reference sequence"). Identity is expressed as the ratio N/D times 100 percent, where N is the number of identical aligned items (bases or amino acids) and D is the sum of the total number of items in the reference sequence and the total individual spaces (corresponding to items in the second sequence) introduced into the reference sequence as a result of its alignment with the second sequence. Further, the alignment by which the N/D ratio of identity is obtained is an alignment which gives essentially the largest possible percentage identity value, i.e., the largest N value (the largest number of aligned sequence items that are identical) and the smallest D value (the smallest number of individual gap spaces introduced into the reference sequence by the alignment). Ascertaining absolutely the highest possible identity value (or best alignment) is not required to report an "essentially largest identity value"0 since this means in the context of the present application that the percentage identity reported has a certainty deviation that limits any possible increases in the identity value due to an alternative alignment to less than one-half of a percentage point. The sequence alignment utilized to obtain the N/D percentage identity may be performed by a manual method (hand and eye alignment) or by utilizing commercially available alignment software. The parameters of the alignment software may be adjusted until an identity value is obtained which has a certainty that limits any increase in the identity value to less than one-half of a percentage point with respect to the reported identity value.

"At Least X Percent Identity" means, as used in the context of the present specification or claims, a comparison with respect to the degree of sameness between a first sequence and a second sequence (the first sequence may also be referred to as the "reference sequence") wherein the degree of sameness is equal to or exceeds the value "X" of the term. The "identity" value (degree of sameness) of this term is expressed as the ratio N/D times 100 percent, where N is the number of identical aligned items (bases or amino acids) and D is the sum of the total number of items in the reference sequence and the total individual spaces (corresponding to items in the second sequence) introduced into the reference sequence as a result of its alignment with the second sequence. If any alignment exists for the second sequence and the reference sequence which results in a sameness value (N/D×100%) that is equal to or greater than the value of "X" in the phrase "at least X percent identity" then the second sequence has "at least X percent identity" with respect to the reference sequence even though it may be possible to align the two sequence in a different manner such that the calculated value is less than X. The sequence alignment utilized to obtain the N/D percentage identity may be performed by a manual method (hand and eye alignment) or by utilizing commercially available alignment software, provided that the "identity" value is calculated as hereinabove described.

Unless otherwise stated, transformation was performed as described in the method of Graham, F. and Van der Eb, A., Virology, 52:456–457 (1973).

The present invention will be further described with reference to the following examples; however, it is to be understood that the present invention is not limited to such examples. All parts or amounts, unless otherwise specified, are by weight.

In order to facilitate understanding of the invention the following examples providing certain frequently occurring methods and/or terms will be described. Such examples are in no way intended to limit the invention disclosed herein to the embodiments described in said examples and it is understood that new and different embodiments will no doubt suggest themselves to those of skill in the art.

EXAMPLE 1

ISOLATING PERV-D POLYNUCLEOTIDE WITH PERV-C PRIMERS

DNA was isolated from the cell line PK-15 (ATCC number CCL-33) using methods known in the art. Primer oligonucleotides were desgned using the Geneworks® 2.5 software program (Oxford Molecular Group, Oxford OX4 4GA, England).

The primer sequence oligonucleotide PalEnvF (SEQ ID NO. 11) was obtained which has the sequence 5' GCC AAC CTC TCA GCA GGA TAG 3' and corresponds to nucleotides 6057–6077 of Genbank Accession Number AF 038600 (Sus scrofa porcine endogenous retrovirus PERV-MSL).

The primer sequence oligonucleotide PalEnvR (SEQ ID NO. 12) has the sequence 5' ATA GCC ATT GGA GGC TCC AG 3' and corresponds to the reverse complement of nucleotides 6325–6344 of Genbank Accession Number AF 038600 (Sus scrofa porcine endogenous retrovirus PERV-MSL).

Such oligonucleotide primers were designed to isolate ERV sequences that are not closely related to PERV-A and PERV-B, since they would not be expected to hybridize to PERVENV1 and PERVENV2 (also described as PERV-A and PERV-B, respectively, Genbank Accession Numbers Y12238 and Y12239, respectively).

About 25 ng of the PK15 genomic DNA was subjected to polymerase chain reaction (PCR) amplification in a 50 μl reaction mixture which included 10 pmoles each of PalEnvF and PalEnvR, 1.5 mM $MgCl_2$, 200 μM dNTP, 1.25 units of Amplitaq Gold (Perkin Elmer, Philadelphia, Pa.). The cycling conditions were 40 cycles, each cycle being incubation at 96° C. for 10 sec., 60° C. for 30 sec, and 72° C. for 30 sec.

From the PCR mixture, about 1 μl was used to ligate the reaction product with pCR™2.1 (Invitrogen TA-Cloning®, Invitrogen, San Diego, Calif.) according to the manufacturer's protocol. The inserted DNA fragments were sequenced using the SequiThermEXCEL™ II DNA sequencing kit (Epicentre Technologies, Inc. Madison, Wis.).

Based upon sequence analysis of 8 independently derived clones, the sequence shown in FIG. 1 was derived. The sequence contained an open reading frame which encoded the polypeptide as shown in FIG. 2. Comparison of the polypeptide sequence to previously described PERV env sequences (FIG. 3) indicates that the sequence shown in FIG. 2 is unique and as such, represents a previously undescribed PERV.

This polynucleotide sequence according to the invention, which has about 79% identity to a portion of PERV-C, is defined as PERV-D.

EXAMPLE 2

ISOLATION OF 5' FRAGMENT OF PERV-DENV REGION

In order to obtain the sequence of the 5' end of the PERV-D env region, DNA was isolated from the porcine kidney cell line, PK-15 (ATCC Number CCL-33) and was subjected to PCR analysis. Two of the forward primers, DA111 SEQ ID NO:13: 5' CACCAACGGCTGTGAAAGTC 3') and DA185 (SEQ ID NO:14: 5' TCTCGTACTTTTGACCACAC 3') are capable of binding to the pol genes of the previously known PERVs (PERV-A and PERV-B described in Le Tissier et al. 1997. *Nature* 389: 681–682 and PERV-C described in Akiyoshi et al. 1998. *Journal of Virology*, 72: 4503–4507) and so had a strong possibility of hybridizing to PERV-D. The reverse primer PERV-D-R2 (SEQ ID NO: 15: 5' GGTTGTCTGTCCCAACCTG 3') is an oligonucleotide that binds to the reverse of SEQ ID NO: 1 nucleotides 200–218 and is specific to PERV-D and use of it would therefore preclude amplification of PERV-A, -B or -C sequences.

PK-15 cells were cultured as recommended by the supplier. Genomic DNA from the cell line was extracted using QIAGEN®'s Genomic-tip 500/G (Qiagen Inc.-USA Valencia, Calif.).

The PCR reaction mixture (volume =50 $\mu$l) contained 25 ng PK-15 genomic DNA. The final reagent mixture included 50 mM KCl, 10 mM Tris-HCl (pH 8.3), 1.5 mM $MgCl_2$, 0.4 mM dNTP and 1.25 units of Amplitaq Gold (Perkin-Elmer Corporation). The PCR primers DA111 (SEQ ID NO: 13) with PERV-D-R2 (SEQ ID NO: 15) or DA185 (SEQ ID NO:14) with PERV-D-R2 (SEQ ID NO: 15) were present at a concentration of 0.2 $\mu$M each.

The reactions were amplified in a Perkin-Elmer GeneAmp 9600 thermal cycler. The initial denaturing step was 9 minutes at 95° C. (also required to activate the "hot-start" Amplitaq Gold) followed by 40 cycles of 96° C. for 10 seconds, 55° C. for 30 seconds and 72° C. for 30 seconds. Thermal cycling was followed by a 5 minute incubation at 72° C. and brought down to 4° C.

The approximately 700 bp PCR products were purified using a Microspin G-50 column (Amersham Pharmacia Biotech). The purified products were TA ligated into the pCR2.1-TOPO vector (Invitrogen, Carlsbad). The ligation reactions were then used to transform competent TOP10 *E.coli*. The cells were incubated on Carb/IPTG/X-gal agar plates and white colonies were selected for further growth in LB broth. Two clones were selected for sequencing: 14-21 9C (PK-15 DNA using DA111 (SEQ ID NO:13) and PERV-D-R2 (SEQ ID NO:15) and 14-21 17 (PK-15 DNA using DA185 (SEQ ID NO: 14) and PERV-D-R2 (SEQ ID NO:15).

Plasmid DNA was extracted from broth cultures using the Wizard miniprep kit (Promega, Madison, Wis.). Sequencing reactions were performed with the SequiThermEXCEL™ DNA sequencing kit (EPICENTRE Technologies, Inc. Madison, Wis.). The sequencing reactions were primed with M13F (SEQ ID NO:16: 5' GTAAAACGACGGCCAG 3') and M13R (SEQ ID NO:17: 5' CAGGAAACAGCTATGAC 3') primers which bind to the pCR2.1-TOPO vector and are directed into the insert. The primers used for amplification were also used to prime sequencing reactions. The radioactively labeled reactions were run out on a 8% PAGE sequencing gel using a BioRad 50 cm×38 cm Sequi-Gen System (BioRad, Hercules, Calif.).

Four additional clones from four individual PCR reactions were also sequenced after duplication of this procedure. The sequence obtained support the data obtained from the first two clones (FIG. 8, SEQ ID NO: 18)

EXAMPLE 3

EXTENSION OF PERV D ENV SEQUENCE INTO THE PROLINE-RICH REGION

Lymphocytes were isolated from the SLA haplotype d/d miniswine #12181 whole blood by centrifugation with Histopaque 1077 (Sigma, St. Louis, Mo.). The porcine kidney cell-line, PK-15 (ATCC Number: CCL-33), was obtained from the ATCC and cultured as recommended. Genomic DNA from both the swine lymphocytes and the cell-line were extracted using QIAGEN's Genomic-tip 500/G.

PCR amplification of genomic DNA extracted from PK-15, cells and from SLA haplotype d/d miniature swine #12181 was performed. Two sets of PCR conditions were used: (1) the PERV-D specific 5' primer PERV-D-F1 (SEQ ID NO:20: 5' GTCATACAGGTACCATTCTGG 3') which corresponds to nucleotides 548–568 from SEQ ID NO: 18) together with the proline region 3' primer TER1 (SEQ ID NO:19 5' GAAAAGCTCCCTGGATGAG 3') which corresponds to the reverse of PERV-C (Genbank Accession Number AF 038600) nucleotides 6475–6493) and (2) PERV-D specific 5' primer PERV-D-F2 (SEQ ID NO:21: 5' GTCAACCCCAATAACCACCG 3') corresponds to nucleotides 517–536 of SEQ ID NO:18 together with TER1 (SEQ ID NO:20). The final reagent mixtures included 25 ng genomic DNA, 50 mM KCl, 10 mM Tris-HCl (pH 8.3), 1.5 mM $MgCl_2$, 0.4 mM dNTP, 2.5 units of Amplitaq Gold (Perkin-Elmer Corporation) and 0.2 $\mu$M each primer in a 50 $\mu$l reaction volume. The reaction was run in a Perkin Elmer 9600 thermal cycler at 94° C. for 9 minutes (to activate TaqGold), then 40 cycles of 96° C. for 10 seconds, 55° C. for 30 seconds, 72° C. for 30 seconds, then an extension at 72° C. for 5 minutes before being brought to a 4° C. hold.

The PCR samples were purified using the Wizard PCR prep kit (Promega, Inc. Madison, Wis.) and TA ligated into the pCR 2.1 TOPO TA clone kit as per the manufacturer's instructions (Invitrogen). Transformation was done with competent TOP10F' *E. coli* cells. The cells were grown overnight on LB/Carb/X-gal/IPTG plates (100×15 mm, VWR).

Colonies were picked and tested for presence of the insert using M13F (SEQ ID NO:16) and M13R (SEQ ID NO:17) primers in a colony PCR. The colonies were spiked into a 50 $\mu$l reaction volume with 50 mM KCl 10 mM Tris-HCl (pH 8.3), 1.5 mM $MgCl_2$, 2 pmol each M13F (SEQ ID NO:16) and M13R (SEQ ID NO:17), and 2.5 Units AmpliTaq Gold (Perkin-Elmer Corporation). The reactions were run for 9 minutes at 96° C., then cycled at 96° C. for 10 sec, 50° C. for 30 sec and 72° C. for four minutes for 35 cycles, held at 72° C. for 5 minutes, then brought down to 4° C.

White colonies were picked and grown overnight in 2 ml LB/carb minicultures at 37° C., shaking. DNA was extracted from the cultures using the Qiagen Spin Miniprep Kit. DNA extracted from 4 clones (3 separate PCR reactions) was sequenced. These clones were 1A and 1C (derived using PK15 cells and the PERV-D-F1 (SEQ ID NO:19)/TER1 (SEQ ID NO:20) primer combination), 2B (derived using miniature swine #12181 DNA and the PERV-D-F1 (SEQ ID NO:19)/TER1 (SEQ ID NO:20) primer combination) and 10B (derived using miniature swine #12181 DNA and the PERV-D-F2 (SEQ ID NO:21/TER1 (SEQ ID NO:20) primer combination).

Sequencing reactions were performed with the SequiThermEXCEL™ DNA sequencing kit (EPICENTRE Technologies, Inc.). The sequencing reactions were primed with M13F (SEQ ID NO:16) and M13R (SEQ ID NO:17) primers. The radioactively labeled reactions were run out on a 8% PAGE sequencing gel using a BioRad 50 cm×38 cm Sequi-Gen System.

The sequence derived is shown in FIG. 9 (SEQ ID NO:22).

EXAMPLE 4

SEQUENCE OF PERV-D 3'ENV THROUGH THE 3'LTR

PCR amplification of miniature swine #12181 DNA (as above) was performed using the PERV-D-F2 (SEQ ID NO:21) and DA189 (SEQ ID NO:23: 5' TTTTCATCCTTTCATTCCCCACTTC 3',) primers. DA189 (SEQ ID NO: 23) corresponds to the reverse complement of PERV C, Genbank accession #AF038600, nucleotides 7575–7599). 10 ng of DNA was added to a 50 µl final reaction volume including 50 mM KCl, 10 mM Tris-HCl (pH 8.3), 1.5 mM MgCl2, 0.4 mM dNTP, 2.5 units of Amplitaq Gold (Perkin-Elmer Corporation), 0.1 µM primer PERV-D-F2 (SEQ ID NO:21), and 0.8 mM primer DA189 (SEQ ID NO:23). The reaction was run in a Perkin Elmer 9600 thermal cycler at 95° C. for 9 minutes, then 96° C. for 10 seconds, 55° C. for 30 seconds and 72° C. for 2 minutes for 40 cycles, held for 5 minutes at 72° C., and brought down to a hold at 4° C.

The PCR product was approximately 1.6 Kb in length, and was purified using the Wizard PCR prep kit (Promega, Inc.). The product was inserted into the pCR2.1 TOPO vector, transformed into competent E. coli TOP10F' cells, and grown on LB/Carb/IPTG/X-Gal plates (100×15mm, VWR) overnight.

Colonies were picked and tested for presence of the insert using primers M13F (SEQ ID NO:16) and M13R (SEQ ID NO:17) as well as the primers PERV-D-F1 (SEQ ID NO:20) and DA189 (SEQ ID NO:23) in a colony PCR. The colonies were spiked into a 50 µl reaction volume with 50 mM KCl, 10 mM Tris-HCl (pH 8.3), 1.5 mM MgCl$_2$, 2 pmol each M13F (SEQ ID NO:16) and M13R (SEQ ID NO:17), and 2.5 Units AmpliTaq Gold (Perkin-Elmer Corporation). The reactions were run for 9 minutes at 96° C., then cycled at 96° C. for 10 sec, 50° C. for 30 sec and 72° C. for four minutes for 35 cycles, held at 72° C. for 5 minutes, then brought down to 4° C. White colonies were picked and grown overnight in 2 ml LB/carb minicultures at 37° C., shaking. DNA was extracted from the cultures using the Qiagen Spin Miniprep Kit.

Two positive clones were chosen and grown overnight in 125 mL LB/Carb, and DNA extracted using the Qiagen PlasmidMaxi Prep DNA Extraction kit with a Qiagen-tip 500 column.

4 µg of the purified DNA was cut with 10 Units of EcoR1 restriction enzyme (N.E.Biolabs, Beverley, Mass.) to check for the presence of the insert. A 20 µg aliquot of Clone 1.A was sent to LARK Technologies, Inc. (Houston, Tex.) for sequencing.

The sequence is shown in FIG. 10.

A contguous sequence was complied from SEQ ID Nos; 18, 22 and 24 to generate SEQ ID NO:25 (FIG. 11).

EXAMPLE 5

ANALYSIS OF A CLONE CONTAINING A 2 KB PERV D FRAGMENT

In order to confirm the sequence of SEQ ID NO: 25 a fragment that extended over the entire 2 Kb region of the PERV-D env region was generated.

PERV D specific primer PERV-D-pol-F (SEQ ID NO:26: 5' AACGGCTGTGAAAGTCGAAAA 3') corresponds to nucleotides 5–25 of SEQ ID NO:18 (PERV-D) and, based upon a DNA alignment of PERV C (Genbank Accession Number AF038600) to the contiguous PERV D DNA sequence, was designed to start 38 bp 5' of the PERV D env start. The primer is identical to the PERV C sequence except at the last 2 bases at the 3' end.

The PERV-D-pol-F primer (SEQ ID NO:26) was used in a PCR reaction with primer DA189 (SEQ ID NO:23), which is not PERV D specific, to amplify full-length PERV D DNA env region sequences. Then 10 ng of PK15 DNA (as described above) was used in a 50 µl reaction with 50 mM KCl, 10 mM Tris-HCl (pH 8.3), 1.5 mM MgCl$_2$, 0.4 mM dNTP, 2.5 units of Amplitaq Gold (Perkin-Elmer Corporation), and 2 ng each of primers PERV-D-pol-F (SEQ ID NO:26) and DA189 (SEQ ID NO:23). The PCR was denatured for 9 minutes at 95° C., then run 10 seconds at 96° C., 30 seconds at 55° C., and 4 minutes at 72° C. for 35 cycles, held at 72° C. for 5 minutes then brought down to a 4° C. hold.

The PCR reactions were cleaned using a Microspin G-50 column (Amersham Pharmacia Biotech) and purified product was ligated into the pCRII TOPO (Invitrogen) vector via the maufacturer's instructions. The ligation mixture was then used to transform competent TOP10F' E. coli cells, which were grown overnight at 37° C. on LB/Carb/IPTG/X-Gal plates (100×15 mm, VWR). Colonies were picked and tested for presence of the insert using M13F (SEQ ID NO:16) and M13R (SEQ ID NO:17) primers in a colony PCR. The colonies were spiked into a 50 µl reaction volume with 50MM KCl, 10 mM Tris-HCl (pH 8.3), 1.5 mM MgCl$_2$, 2 pmol each M13F (SEQ ID NO:16) and M13R (SEQ ID NO:17, and 2.5 Units AmpliTaq Gold (Perkin-Elmer Corporation). The reactions were run for 9 minutes at 96° C., then cycled at 96° C. for 10 sec, 50° C. for 30 sec and 72° C. for four minutes for 35 cycles, held at 72° C. for 5 minutes, then brought down to 4° C. The desired band was approximately 2.2 Kb. The pCRII.1-TOPO vector containing porcine DNA 2 kb insert PERV-D3F was deposited with the ATCC and assigned number PTA-468.

Two positive samples were grown overnight in 1.5 mL LB/Carb minicultures, then extracted using the Qiagen MiniPrep DNA Extraction kit. The clones were quantitated by spectrophotometry, then cut with 10 Units of SacI restriction enzyme. Clone 3F was prepared for sequencing on a Beckman CEQ2000 DNA sequencer using the manufacturer's instructions and reagents.

This 2 Kb DNA was sequenced with 9 total primers. These primers were M13R (SEQ ID NO: 17), PERV-D-pol-F (SEQ ID NO:26), PERV-D-R2 (SEQ ID NO:15), PERV-D-F1 (SEQ ID NO:20), DA176 (SEQ ID NO:27 corresponds to the reverse complement of Genbank accession number AF038600 nucleotides 6762–6785), DA158 SEQ ID NO 28 (5' AGTAGTTTCCTTTTCCCTTC- GACGCTTC which corresponds to the reverse complement of Genbank accession number AF038600 nucleotides 7290–7317), DA189 (SEQ ID NO:23) and –47 (SEQ ID NO:29: 5' CGCCAGGGTTTCCCAGTCACGAC 3', a primer which binds to the PCRII TOPO vector).

The sequence of the PERV-D env region (SEQ ID NO: 30) is shown in FIG. 12. A comparison of SEQ ID NO:25 and SEQ ID NO: 30 showed them to be 100% identical.

By comparison to other PERV env coding regions, the predicted env coding region starts with the codon AUA (nucleotides 43–45) rather than with a methionine ATG. The PERV-D 3F clone env Consensus (SEQ ID NO: 30) sequence has an open reading frame (ORF) from the start of the env until nucleotide 1735. The presence of an inserted T results in a frameshift.

A comparison of thePERV-D sequence (SEQ ID NO:30) to the env region of PERV-C (Genbank Accession number AF038600) is presented in FIG. 12.

A comparison of the PERV-D and PERV-C env region sequences is presented in FIG. 13. Over the 2009 nucleotide region which includes gaps to optimize the alignment there are 197 nucleotide differences, or in other words, the sequences share 90% identity. The longest length of complete sequence identity between the two sequences is 113 nucleotides.

EXAMPLE 6

ASSAY THAT SPECIFICALLY DETECTS THE PRESENCE OF PERV D SEQUENCES

Four sets of primers were used to test the primer specificity:

PERV-D-pol-F (SEQ ID NO:26) is PERV-D specific and located 5' of the env start. ALR-4 (SEQ ID NO: 31: 5' CGGTGGTTATTGGGGTTGAC 3') is a PERV-D specific primer designed to be the reverse-complement to PERV-D-F2 (SEQ ID NO:21). SEQ ID NO:21 is located at nucleotides 512–533 from the start of PERV-D env. PalEnvF (SEQ ID NO:32: 5' CCAACCTCTCTGCAGGATAG 3') is a PERV-C/D specific primer corresponding to the region of nucleotides 6100–6120 of PERV C (Genbank Accession Number AF038600 and to nucleotides 481–500 of SEQ ID NO: 30.

DA185 (SEQ ID NO:14) is PERV-C/D specific and corresponds to nucleotides 5561–5580 of PERV-C (Genbank Accession Number AF038600). This is 59 bp before the start of PERV-C and PERV-D env coding sequence.

PalEnvR (SEQ ID NO:33 5' ATAGCCATTGGAGGCTC-CAG 3') is also PERV-C/D specific and corresponds to the reverse complement of Genbank Accession number AF038600 nucleotides 6325–6344. With one mismatch the sequence corresponds to the reverse complement of 736–755 of SEQ ID NO:30.

Primers were used in the following configurations: PERV D Pol F/ALR 4, PERV D Pol F/Pal Env R, DA185/Pal Env R, Pal Env F/Pal Env R.

The samples included:

1. DNA from 293 cells chronically infected with a single particle clone of either PERV A or PERV B (2A2.A, 2A2.B, respectively, obtained from Professor Robin Weiss, London). High molecular weight DNA was obtained by phenol/chloroform/iso-amyl-alcohol extraction and brought up in 10 mM Tris-HCl in 1 mM EDTA buffer to a concentration of 100 ng/µl.

2. A retroviral vector described as Neptune 6 which contains a full-length PERV C clone. DNA dilution 3A (1000 copies/5 µl).

3. PK15 DNA which contains both PERV-C and PERV-D sequences.

PCR was performed using a Perkin-Elmer 9600 using a 50 µl total reaction volume. 50 mM KCl, 10 mM Tris-HCl (pH 8.3), 1.5 mM MgCl$_2$, 0.4 mM dNTP and 1.25 units of Amplitaq Gold (Perkin-Elmer Corporation) were present in each tube. Primers were present in the following concentrations per tube: PERV-D-pol-F1 (SEQ ID NO:26) 100 ng; ALR-4 (SEQ ID NO:31) 100 ng; DA185 (SEQ ID NO:14) 100 ng; PalEnvF (SEQ ID NO:32) 40 µM (approx 100 ng); PalEnvR (SEQ ID NO:33) 40 µM (approx 100 ng).

Cycling Parameters: 9 minutes at 95° C., 35 cycles (96° C. for 10 sec, 55° C. for 30 seconds, 72° C. for 30 seconds), 5 minutes at 72° C., hold at 4° C.

Expected band sizes: PERVDPol F/ALR-4 543 bp

PERV-D-pol-F/PalEnvR 762 bp

DA185/PalEnvR 783 bp PERV-D, 771 bp PERV-C

PalEnvF/PalEnvR 276 bp PERV-D, 264 bp PERV-C

It can be seen from FIG. 14 that either of the two primer combinations (PERV-D-pol-F/ALR 4 and PERV-D-pol-F/PalEnvR) can be successfully used to distinguish PERV-D sequences from PERV-A, -B, or -C sequences. The results are tabulated in Table 1.

TABLE 1

RESULTS FROM PCR AMPLIFICATION OF PERV A, B, C, D SAMPLES

| Primer Pair | Specificity | PERV A | PERV B | PERV C | PERV D |
|---|---|---|---|---|---|
| PERV-D-pol-F/ ALR 4 | PERV-D/ PERV-D | Negative | Negative | Negative | Positive |
| PERV-D-pol-F/ PalEnvR | PERV-D/ PERV-C + D | Negative | Negative | Negative | Positive |
| DA185/ PalEnvR | PERVC + D/ PERV C + D | Negative | Negative | Positive | Positive |
| PalEnvF/ PalEnvR | PERV-C + D/PERV-C + D | Negative | Negative | Positive | Positive |

What is claimed is:

1. An isolated polynucleotide, comprising:

a first polynucleotide having at least 95% identity to a second polynucleotide encoding a PERV-D polypeptide comprising SEQ ID NO: 2 wherein said first polynucleotide encodes at least one immunogenic fragment specific to said PERV-D polypeptide; or the full complement of said first polynucleotide.

2. The isolated polynucleotide of claim 1, wherein said isolated polynucleotide comprises said first polynucleotide.

3. A method of making a recombinant vector comprising inserting the isolated polynucleotide of claim 2 into a vector wherein the isolated polynucleotide is DNA.

4. A recombinant vector comprising the isolated polynucleotide of claim 2, wherein the isolated polynucleotide is DNA.

5. A recombinant host cell comprising the isolated polynucleotide of claim 2 wherein said isolated polynucleotide is DNA.

6. The isolated polynucleotide of claim 2 wherein said first polynucleotide encodes a polypeptide consisting of SEQ ID NO:2.

7. A method for producing a polypeptide comprising expressing from the recombinant cell of claim 5 the polypeptide encoded by said isolated polynucleotide.

8. An isolated polynucleotide, comprising:

a first polynucleotide having at least 95% identity to a member selected from the group consisting of:
  (a) a second polynucleotide comprising the sequence shown as SEQ ID NO: 1; and
  (b) the full complement of (a).

9. The isolated polynucleotide of claim 8, wherein said member is (a).

10. A method of making a recombinant vector comprising inserting the isolated polynucleotide of claim 9 into a vector, wherein said isolated polynucleotide is DNA.

11. A recombinant vector comprising the isolated polynucleotide of claim 9 wherein said isolated polynucleotide is DNA.

12. A recombinant host cell comprising the isolated polynucleotide of claim 9 wherein said isolated polynucleotide is DNA.

13. The isolated polynucleotide of claim 9 wherein said first polynucleotide consists of SEQ ID NO:1.

14. A method for producing a polypeptide, comprising expressing from the recombinant cell of claim 12 the polypeptide encoded by said isolated polynucleotide, wherein said first polynucleotide encodes at least one immunogenic fragment specific to PERV-D polypeptide.

15. A method for producing a polypeptide, comprising expressing from the recombinant cell of claim 12 the polypeptide encoded by SEQ ID NO: 1.

* * * * *

UNITED STATES PATENT AND TRADEMARK OFFICE
CERTIFICATE OF CORRECTION

PATENT NO. : 6,261,806 B1
DATED : July 17, 2001
INVENTOR(S) : Banerjee et al.

It is certified that error appears in the above-identified patent and that said Letters Patent is hereby corrected as shown below:

Column 1,
Line 51, delete "veterinary" and insert therefor -- Veterinary --

Column 13,
Line 50, delete "procine" and insert therefor -- porcine --

Column 17,
Line 2, delete "is"
Line 33, delete "0"

Column 18,
Line 28, delete "desgned" and insert therefor -- designed --

Column 22,
Line 2, delete "contguous" and insert therefor -- contiguous --
Line 2, delete "complied" and insert therefor -- compiled --
Line 44, delete "55 MM" and insert therefor -- 55 mM --

Column 23,
Line 5, delete "PCRII" and insert therefor -- pCRII --
Line 16, delete "thePERV-D" and insert therefor -- the PERV-D --

Signed and Sealed this

Seventh Day of May, 2002

*Attest:*

JAMES E. ROGAN
*Director of the United States Patent and Trademark Office*

*Attesting Officer*

SEQUENCE LISTING

<160> NUMBER OF SEQ ID NOS: 33

<210> SEQ ID NO 1
<211> LENGTH: 275
<212> TYPE: DNA
<213> ORGANISM: Artificial Sequence
<220> FEATURE:
<223> OTHER INFORMATION: Description of Artificial Sequence:cDNA coding
      for a PERV-D env polypeptide

<400> SEQUENCE: 1

```
ccaacctctc agcaggatag ggtaagcttt tcttatgtca accccaataa ccaccggacc      60
tggaaaacgt catacaggta ccattctggg tgttttccct cagacctaga ttatcttaaa    120
ataagtttca ccgaaaaaaa aaaacaagaa aatatcctaa aatggataaa tggtatgtcc    180
tggggaataa tatattatac aggttgggac agacaaccag gctccattct aaccatccga    240
cttaaaataa gccagctgga gcctccaatg gctat                                275
```

<210> SEQ ID NO 2
<211> LENGTH: 91
<212> TYPE: PRT
<213> ORGANISM: Artificial Sequence
<220> FEATURE:
<223> OTHER INFORMATION: Description of Artificial Sequence:Deduced
      polypeptide sequence derived from the cDNA of SEQ
      ID NO: 1.

<400> SEQUENCE: 2

```
Pro Thr Ser Gln Gln Asp Arg Val Ser Phe Ser Tyr Val Asn Pro Asn
 1               5                  10                  15

Asn His Arg Thr Trp Lys Thr Ser Tyr Arg Tyr His Ser Gly Cys Phe
                20                  25                  30

Pro Ser Asp Leu Asp Tyr Leu Lys Ile Ser Phe Thr Glu Lys Lys Lys
            35                  40                  45

Gln Glu Asn Ile Leu Lys Trp Ile Asn Gly Met Ser Trp Gly Ile Ile
        50                  55                  60

Tyr Tyr Thr Gly Trp Asp Arg Gln Pro Gly Ser Ile Leu Thr Ile Arg
 65                  70                  75                  80

Leu Lys Ile Ser Gln Leu Glu Pro Pro Met Ala
                85                  90
```

<210> SEQ ID NO 3
<211> LENGTH: 656
<212> TYPE: PRT
<213> ORGANISM: Artificial Sequence
<220> FEATURE:
<223> OTHER INFORMATION: Description of Artificial Sequence:Amino acid
      sequence of a PERV env polypeptide previously
      described

<400> SEQUENCE: 3

```
Met His Pro Thr Leu Ser Arg Arg His Leu Pro Thr Arg Gly Gly Glu
 1               5                  10                  15

Pro Lys Arg Leu Arg Ile Pro Leu Ser Phe Ala Ser Ile Ala Trp Phe
                20                  25                  30

Leu Thr Leu Thr Ile Thr Pro Gln Ala Ser Ser Lys Arg Leu Ile Asp
            35                  40                  45

Ser Ser Asn Pro His Arg Pro Leu Ser Leu Thr Trp Leu Ile Ile Asp
        50                  55                  60
```

-continued

```
Pro Asp Thr Gly Val Thr Val Asn Ser Thr Arg Gly Val Ala Pro Arg
 65                  70                  75                  80

Gly Thr Trp Trp Pro Glu Leu His Phe Cys Leu Arg Leu Ile Asn Pro
                 85                  90                  95

Ala Val Lys Ser Thr Pro Pro Asn Leu Val Arg Ser Tyr Gly Phe Tyr
            100                 105                 110

Cys Cys Pro Gly Thr Glu Lys Glu Lys Tyr Cys Gly Gly Ser Gly Glu
        115                 120                 125

Ser Phe Cys Arg Arg Trp Ser Cys Val Thr Ser Asn Asp Gly Asp Trp
    130                 135                 140

Lys Trp Pro Ile Ser Leu Gln Asp Arg Val Lys Phe Ser Phe Val Asn
145                 150                 155                 160

Ser Gly Pro Gly Lys Tyr Lys Met Met Lys Leu Tyr Lys Asp Lys Ser
                165                 170                 175

Cys Ser Pro Ser Asp Leu Asp Tyr Leu Lys Ile Ser Phe Thr Glu Arg
            180                 185                 190

Lys Thr Gly Lys Tyr Ser Lys Val Asp Lys Trp Tyr Glu Leu Gly Asn
        195                 200                 205

Ser Phe Leu Leu Tyr Gly Gly Ala Gly Ser Thr Leu Thr Ile Arg
    210                 215                 220

Leu Arg Ile Glu Thr Gly Thr Glu Pro Pro Val Ala Met Gly Pro Asp
225                 230                 235                 240

Lys Val Leu Ala Glu Gln Gly Pro Pro Ala Leu Glu Pro Pro His Asn
                245                 250                 255

Leu Pro Val Pro Gln Leu Thr Ser Leu Arg Pro Asp Ile Thr Gln Pro
            260                 265                 270

Pro Ser Asn Ser Thr Thr Gly Leu Ile Pro Thr Asn Thr Pro Arg Asn
        275                 280                 285

Ser Pro Gly Val Pro Val Lys Thr Gly Gln Arg Leu Phe Ser Leu Ile
    290                 295                 300

Gln Gly Ala Phe Gln Ala Ile Asn Ser Thr Asp Pro Asp Ala Thr Ser
305                 310                 315                 320

Ser Cys Trp Leu Cys Leu Ser Ser Gly Pro Pro Tyr Tyr Glu Gly Met
                325                 330                 335

Ala Lys Glu Arg Lys Phe Asn Val Thr Lys Glu His Arg Asn Gln Cys
            340                 345                 350

Thr Trp Gly Ser Arg Asn Lys Leu Thr Leu Thr Glu Val Ser Gly Lys
        355                 360                 365

Gly Thr Cys Ile Gly Lys Ala Pro Pro Ser His Gln His Leu Cys Tyr
    370                 375                 380

Ser Thr Val Val Tyr Glu Gln Ala Ser Glu Asn Gln Tyr Leu Val Pro
385                 390                 395                 400

Gly Tyr Asn Arg Trp Trp Ala Cys Asn Thr Gly Leu Thr Pro Cys Val
                405                 410                 415

Ser Thr Ser Val Phe Asn Gln Ser Lys Asp Phe Cys Val Met Val Gln
            420                 425                 430

Ile Val Pro Arg Val Tyr Tyr His Pro Glu Glu Val Val Leu Asp Glu
        435                 440                 445

Tyr Asp Tyr Arg Tyr Asn Arg Pro Lys Arg Glu Pro Val Ser Leu Thr
    450                 455                 460

Leu Ala Val Met Leu Gly Leu Gly Thr Ala Val Gly Val Gly Thr Gly
465                 470                 475                 480
```

```
Thr Ala Ala Leu Ile Thr Gly Pro Gln Gln Leu Glu Lys Gly Leu Gly
                485                 490                 495

Glu Leu His Ala Ala Met Thr Glu Asp Leu Arg Ala Leu Lys Glu Ser
            500                 505                 510

Val Ser Asn Leu Glu Glu Ser Leu Thr Ser Leu Ser Glu Val Val Leu
            515                 520                 525

Gln Asn Arg Arg Gly Leu Asp Leu Leu Phe Leu Arg Glu Gly Gly Leu
        530                 535                 540

Cys Ala Ala Leu Lys Glu Glu Cys Cys Phe Tyr Val Asp His Ser Gly
545                 550                 555                 560

Ala Ile Arg Asp Ser Met Asn Lys Leu Arg Lys Leu Glu Arg Arg
                565                 570                 575

Arg Arg Glu Arg Glu Ala Asp Gln Gly Trp Phe Glu Gly Trp Phe Asn
            580                 585                 590

Arg Ser Pro Trp Met Thr Thr Leu Leu Ser Ala Leu Thr Gly Pro Leu
            595                 600                 605

Val Val Leu Leu Leu Leu Leu Thr Val Gly Pro Cys Leu Ile Asn Arg
            610                 615                 620

Phe Val Ala Phe Val Arg Glu Arg Val Ser Ala Val Gln Ile Met Val
625                 630                 635                 640

Leu Arg Gln Gln Tyr Gln Gly Leu Leu Ser Gln Gly Glu Thr Asp Leu
                645                 650                 655

<210> SEQ ID NO 4
<211> LENGTH: 657
<212> TYPE: PRT
<213> ORGANISM: Artificial Sequence
<220> FEATURE:
<223> OTHER INFORMATION: Description of Artificial Sequence:PERV-B
      polypeptide sequence taken for comparison from
      GenBank Accession No. Y12239.

<400> SEQUENCE: 4

Met His Pro Thr Leu Ser Trp Arg His Leu Pro Thr Arg Gly Gly Glu
  1               5                  10                  15

Pro Lys Arg Leu Arg Ile Pro Leu Ser Phe Ala Ser Ile Ala Trp Phe
                20                  25                  30

Leu Thr Leu Thr Ile Thr Pro Gln Ala Ser Ser Lys Arg Leu Ile Asp
            35                  40                  45

Ser Ser Asn Pro His Arg Pro Leu Ser Leu Thr Trp Leu Ile Ile Asp
        50                  55                  60

Pro Asp Thr Gly Val Thr Val Asn Ser Thr Arg Gly Val Ala Pro Arg
65                  70                  75                  80

Gly Thr Trp Trp Pro Glu Leu His Phe Cys Leu Arg Leu Ile Asn Pro
                85                  90                  95

Ala Val Lys Ser Thr Pro Pro Asn Leu Val Arg Ser Tyr Gly Phe Tyr
            100                 105                 110

Cys Cys Pro Gly Thr Glu Lys Glu Lys Tyr Cys Gly Gly Ser Gly Glu
        115                 120                 125

Ser Phe Cys Arg Arg Trp Ser Cys Val Thr Ser Asn Asp Gly Asp Trp
    130                 135                 140

Lys Trp Pro Ile Ser Leu Gln Asp Arg Val Lys Phe Ser Phe Val Asn
145                 150                 155                 160

Ser Gly Pro Gly Lys Tyr Lys Val Met Lys Leu Tyr Lys Asp Lys Ser
                165                 170                 175
```

-continued

```
Cys Ser Pro Ser Asp Leu Asp Tyr Leu Lys Ile Ser Phe Thr Glu Lys
            180                 185                 190

Gly Lys Gln Glu Asn Ile Gln Lys Trp Ile Asn Gly Met Ser Trp Gly
            195                 200                 205

Ile Val Phe Tyr Lys Tyr Gly Gly Ala Gly Ser Thr Leu Thr Ile
            210                 215                 220

Arg Leu Arg Ile Glu Thr Gly Thr Glu Pro Pro Val Ala Val Gly Pro
225                 230                 235                 240

Asp Lys Val Leu Ala Glu Gln Gly Pro Pro Ala Leu Glu Pro Pro His
            245                 250                 255

Asn Leu Pro Val Pro Gln Leu Thr Ser Leu Arg Pro Asp Ile Thr Gln
            260                 265                 270

Pro Pro Ser Asn Gly Thr Thr Gly Leu Ile Pro Thr Asn Thr Pro Arg
            275                 280                 285

Asn Ser Pro Gly Val Pro Val Lys Thr Gly Gln Arg Leu Phe Ser Leu
            290                 295                 300

Ile Gln Gly Ala Phe Gln Ala Ile Asn Ser Thr Asp Pro Asp Ala Thr
305                 310                 315                 320

Ser Ser Cys Trp Leu Cys Leu Ser Ser Gly Pro Pro Tyr Tyr Glu Gly
            325                 330                 335

Met Ala Lys Glu Gly Lys Phe Asn Val Thr Lys Glu His Arg Asn Gln
            340                 345                 350

Cys Thr Trp Gly Ser Arg Asn Lys Leu Thr Leu Thr Glu Val Ser Gly
            355                 360                 365

Lys Gly Thr Cys Ile Gly Lys Ala Pro Pro Ser His Gln His Leu Cys
            370                 375                 380

Tyr Ser Thr Val Val Tyr Glu Gln Ala Ser Glu Asn Gln Tyr Leu Val
385                 390                 395                 400

Pro Gly Tyr Asn Arg Trp Trp Ala Cys Asn Thr Gly Leu Thr Pro Cys
            405                 410                 415

Val Ser Thr Ser Val Phe Asn Gln Ser Lys Asp Phe Cys Val Met Val
            420                 425                 430

Gln Ile Val Pro Arg Val Tyr Tyr His Pro Glu Glu Val Leu Asp
            435                 440                 445

Glu Tyr Asp Tyr Arg Tyr Asn Arg Pro Lys Arg Glu Pro Val Ser Leu
450                 455                 460

Thr Leu Ala Val Met Leu Gly Leu Gly Thr Ala Val Gly Val Gly Thr
465                 470                 475                 480

Gly Thr Ala Ala Leu Ile Thr Gly Pro Gln Gln Leu Glu Lys Gly Leu
            485                 490                 495

Gly Glu Leu His Ala Ala Met Thr Glu Asp Leu Arg Ala Leu Glu Glu
            500                 505                 510

Ser Val Ser Asn Leu Glu Glu Ser Leu Thr Ser Leu Ser Glu Val Val
            515                 520                 525

Leu Gln Asn Arg Arg Gly Leu Asp Leu Leu Phe Leu Arg Glu Gly Gly
            530                 535                 540

Leu Cys Ala Ala Leu Lys Glu Glu Cys Cys Phe Tyr Val Asp His Ser
545                 550                 555                 560

Gly Ala Ile Arg Asp Ser Met Ser Lys Leu Arg Glu Arg Leu Glu Arg
            565                 570                 575

Arg Arg Arg Glu Arg Glu Ala Asp Gln Gly Trp Phe Glu Gly Trp Phe
            580                 585                 590
```

-continued

```
Asn Arg Ser Pro Trp Met Thr Thr Leu Leu Ser Ala Leu Thr Gly Pro
        595                 600                 605
Leu Val Val Leu Leu Leu Leu Thr Val Gly Pro Cys Leu Ile Asn
    610                 615                 620
Arg Phe Val Ala Phe Val Arg Glu Arg Val Ser Ala Val Gln Ile Met
625                 630                 635                 640
Val Leu Arg Gln Gln Tyr Gln Gly Leu Leu Ser Gln Gly Glu Thr Asp
                645                 650                 655
Leu
```

<210> SEQ ID NO 5
<211> LENGTH: 660
<212> TYPE: PRT
<213> ORGANISM: Artificial Sequence
<220> FEATURE:
<223> OTHER INFORMATION: Description of Artificial Sequence:PERV-A
    polypeptide sequence taken from GenBank Accession
    No. Y12238 for comparison.

<400> SEQUENCE: 5

```
Met His Pro Thr Leu Ser Arg Arg His Leu Pro Ile Arg Gly Gly Lys
  1               5                  10                  15
Pro Lys Arg Leu Lys Ile Pro Leu Ser Phe Ala Ser Ile Ala Trp Phe
                 20                  25                  30
Leu Thr Leu Ser Ile Thr Pro Gln Val Asn Gly Lys Arg Leu Val Asp
             35                  40                  45
Ser Pro Asn Ser His Lys Pro Leu Ser Leu Thr Trp Leu Leu Thr Asp
     50                  55                  60
Ser Gly Thr Gly Ile Asn Ile Asn Ser Thr Gln Gly Glu Ala Pro Leu
 65                  70                  75                  80
Gly Thr Trp Trp Pro Glu Leu Tyr Val Cys Leu Arg Ser Val Ile Pro
                 85                  90                  95
Gly Leu Asn Asp Gln Ala Thr Pro Pro Asp Val Leu Arg Ala Tyr Gly
            100                 105                 110
Phe Tyr Val Cys Pro Gly Pro Pro Asn Asn Glu Glu Tyr Cys Gly Asn
            115                 120                 125
Pro Gln Asp Phe Phe Cys Lys Gln Trp Ser Cys Ile Thr Ser Asn Asp
    130                 135                 140
Gly Asn Trp Lys Trp Pro Val Ser Gln Gln Asp Arg Val Ser Tyr Ser
145                 150                 155                 160
Phe Val Asn Asn Pro Thr Ser Tyr Asn Gln Phe Asn Tyr Gly His Gly
                165                 170                 175
Arg Trp Lys Asp Trp Gln Gln Arg Val Gln Lys Asp Val Arg Asn Lys
            180                 185                 190
Gln Ile Ser Cys His Ser Leu Asp Leu Asp Tyr Leu Lys Ile Ser Phe
        195                 200                 205
Thr Glu Lys Gly Lys Gln Glu Asn Ile Gln Lys Trp Val Asn Gly Ile
    210                 215                 220
Ser Trp Gly Ile Val Tyr Tyr Gly Gly Ser Gly Arg Lys Lys Gly Ser
225                 230                 235                 240
Val Leu Thr Ile Arg Leu Arg Ile Glu Thr Gln Met Glu Pro Pro Val
                245                 250                 255
Ala Ile Gly Pro Asn Lys Gly Leu Ala Glu Gln Gly Pro Pro Ile Gln
            260                 265                 270
Glu Gln Arg Pro Ser Pro Asn Pro Ser Asp Tyr Asn Thr Thr Ser Gly
        275                 280                 285
```

-continued

```
Ser Val Pro Thr Glu Pro Asn Ile Thr Ile Lys Thr Gly Ala Lys Leu
    290                 295                 300

Phe Ser Leu Ile Gln Gly Ala Phe Gln Ala Leu Asn Ser Thr Thr Pro
305                 310                 315                 320

Glu Ala Thr Ser Ser Cys Trp Leu Cys Leu Ala Ser Gly Pro Pro Tyr
                325                 330                 335

Tyr Glu Gly Met Ala Arg Gly Gly Lys Phe Asn Val Thr Lys Glu His
                340                 345                 350

Arg Asp Gln Cys Thr Trp Gly Ser Gln Asn Lys Leu Thr Leu Thr Glu
            355                 360                 365

Val Ser Gly Lys Gly Thr Cys Ile Gly Met Val Pro Pro Ser His Gln
    370                 375                 380

His Leu Cys Asn His Thr Glu Ala Phe Asn Arg Thr Ser Glu Ser Gln
385                 390                 395                 400

Tyr Leu Val Pro Gly Tyr Asp Arg Trp Trp Ala Cys Asn Thr Gly Leu
                405                 410                 415

Thr Pro Cys Val Ser Thr Leu Val Phe Asn Gln Thr Lys Asp Phe Cys
                420                 425                 430

Val Met Val Gln Ile Val Pro Arg Val Tyr Tyr Pro Glu Lys Ala
            435                 440                 445

Val Leu Asp Glu Tyr Asp Tyr Arg Tyr Asn Arg Pro Lys Arg Glu Pro
    450                 455                 460

Ile Ser Leu Thr Leu Ala Val Met Leu Gly Leu Gly Val Ala Ala Gly
465                 470                 475                 480

Val Gly Thr Gly Thr Ala Ala Leu Ile Thr Gly Pro Gln Gln Leu Glu
                485                 490                 495

Lys Gly Leu Ser Asn Leu His Arg Ile Val Thr Glu Asp Leu Gln Ala
                500                 505                 510

Leu Glu Lys Ser Val Ser Asn Leu Glu Glu Ser Leu Thr Ser Leu Ser
            515                 520                 525

Glu Val Val Leu Gln Asn Arg Arg Gly Leu Asp Leu Leu Phe Leu Lys
    530                 535                 540

Glu Gly Gly Leu Cys Val Ala Leu Lys Glu Glu Cys Cys Phe Tyr Val
545                 550                 555                 560

Asp His Ser Gly Ala Ile Arg Asp Ser Met Ser Lys Leu Arg Glu Arg
                565                 570                 575

Leu Glu Arg Arg Arg Arg Glu Arg Glu Ala Asp Gln Gly Trp Phe Glu
            580                 585                 590

Gly Trp Phe Asn Arg Ser Pro Trp Met Thr Thr Leu Leu Ser Ala Leu
    595                 600                 605

Thr Gly Pro Leu Val Val Leu Leu Leu Leu Thr Val Gly Pro Cys
610                 615                 620

Leu Ile Asn Arg Phe Val Ala Phe Val Arg Glu Arg Val Ser Ala Val
625                 630                 635                 640

Gln Ile Met Val Leu Arg Gln Gln Tyr Gln Gly Leu Leu Ser Gln Gly
                645                 650                 655

Glu Thr Asp Leu
            660

<210> SEQ ID NO 6
<211> LENGTH: 638
<212> TYPE: PRT
<213> ORGANISM: Artificial Sequence
```

<220> FEATURE:
<223> OTHER INFORMATION: Description of Artificial Sequence:PERV-C
      polypeptide sequence taken from GenBank Accession
      No. AF038600 for comparison.

<400> SEQUENCE: 6

```
Met His Pro Thr Leu Asn Arg Arg His Leu Pro Ile Arg Gly Gly Lys
 1               5                  10                  15

Pro Lys Arg Leu Lys Ile Pro Leu Ser Phe Ala Ser Ile Ala Trp Phe
                20                  25                  30

Leu Thr Leu Ser Ile Thr Ser Gln Thr Asn Gly Met Arg Ile Gly Asp
            35                  40                  45

Ser Leu Asn Ser His Lys Pro Leu Ser Leu Thr Trp Leu Ile Thr Asp
     50                  55                  60

Ser Gly Thr Gly Ile Asn Ile Asn Asn Thr Gln Gly Glu Ala Pro Leu
 65                  70                  75                  80

Gly Thr Trp Trp Pro Asp Leu Tyr Val Cys Leu Arg Ser Val Ile Pro
                 85                  90                  95

Ser Leu Thr Ser Pro Pro Asp Ile Leu His Ala His Gly Phe Tyr Val
                100                 105                 110

Cys Pro Gly Pro Pro Asn Asn Gly Lys His Cys Gly Asn Pro Arg Asp
                115                 120                 125

Phe Phe Cys Lys Gln Trp Asn Cys Val Thr Ser Asn Asp Gly Tyr Trp
130                 135                 140

Lys Trp Pro Thr Ser Gln Gln Asp Arg Val Ser Phe Ser Tyr Val Asn
145                 150                 155                 160

Thr Tyr Thr Ser Ser Gly Gln Phe Asn Tyr Leu Thr Trp Ile Arg Thr
                165                 170                 175

Gly Ser Pro Lys Cys Ser Pro Ser Asp Leu Asp Tyr Leu Lys Ile Ser
                180                 185                 190

Phe Thr Glu Lys Gly Lys Gln Glu Asn Ile Leu Lys Trp Val Asn Gly
            195                 200                 205

Met Ser Trp Gly Met Val Tyr Tyr Gly Gly Ser Gly Lys Gln Pro Gly
        210                 215                 220

Ser Ile Leu Thr Ile Arg Leu Lys Ile Asn Gln Leu Glu Pro Pro Met
225                 230                 235                 240

Ala Ile Gly Pro Asn Thr Val Leu Thr Gly Gln Arg Pro Pro Thr Gln
                245                 250                 255

Gly Pro Gly Pro Ser Ser Asn Ile Thr Ser Gly Ser Asp Pro Thr Glu
                260                 265                 270

Ser Ser Ser Thr Thr Lys Met Gly Ala Lys Leu Phe Ser Leu Ile Gln
            275                 280                 285

Gly Ala Phe Gln Ala Leu Asn Ser Thr Thr Pro Glu Ala Thr Ser Ser
        290                 295                 300

Cys Trp Leu Cys Leu Ala Ser Gly Pro Pro Tyr Tyr Glu Gly Met Ala
305                 310                 315                 320

Arg Arg Gly Lys Phe Asn Val Thr Lys Glu His Arg Asp Gln Cys Thr
                325                 330                 335

Trp Gly Ser Gln Asn Lys Leu Thr Leu Thr Glu Val Ser Gly Lys Gly
            340                 345                 350

Thr Cys Ile Gly Lys Val Pro Pro Ser His Gln His Leu Cys Asn His
        355                 360                 365

Thr Glu Ala Phe Asn Gln Thr Ser Glu Ser Gln Tyr Leu Val Pro Gly
    370                 375                 380
```

-continued

| | | | | | | | | | | | | | | |
|---|---|---|---|---|---|---|---|---|---|---|---|---|---|---|
|Tyr|Asp|Arg|Trp|Trp|Ala|Cys|Asn|Thr|Gly|Leu|Thr|Pro|Cys|Val|Ser|
|385| | | |390| | | |395| | | |400| | |

Thr Leu Val Phe Asn Gln Thr Lys Asp Phe Cys Ile Met Val Gln Ile
                405                 410                 415

Val Pro Arg Val Tyr Tyr Pro Glu Lys Ala Ile Leu Asp Glu Tyr
                420             425                 430

Asp Tyr Arg Asn His Arg Gln Lys Arg Glu Pro Ile Ser Leu Thr Leu
            435                 440                 445

Ala Val Met Leu Gly Leu Gly Val Ala Ala Gly Val Gly Thr Gly Thr
450                 455                 460

Ala Ala Leu Val Thr Gly Pro Gln Gln Leu Glu Thr Gly Leu Ser Asn
465                 470                 475                 480

Leu His Arg Ile Val Thr Glu Asp Leu Gln Ala Leu Glu Lys Ser Val
                485                 490                 495

Ser Asn Leu Glu Glu Ser Leu Thr Ser Leu Ser Glu Val Val Leu Gln
            500                 505                 510

Asn Arg Arg Gly Leu Asp Leu Leu Phe Leu Lys Glu Gly Gly Leu Cys
        515                 520                 525

Val Ala Leu Lys Glu Glu Cys Cys Phe Tyr Val Asp His Ser Gly Ala
    530                 535                 540

Ile Arg Asp Ser Met Asn Lys Leu Arg Glu Arg Leu Glu Lys Arg Arg
545                 550                 555                 560

Arg Glu Lys Glu Thr Thr Gln Gly Trp Phe Glu Gly Trp Phe Asn Arg
                565                 570                 575

Ser Leu Trp Leu Ala Thr Leu Leu Ser Ala Leu Thr Gly Pro Leu Ile
                580                 585                 590

Val Leu Leu Leu Leu Leu Thr Val Gly Pro Cys Ile Ile Asn Lys Leu
            595                 600                 605

Ile Ala Phe Ile Arg Glu Arg Ile Ser Ala Val Gln Ile Met Val Leu
        610                 615                 620

Arg Gln Gln Tyr Gln Ser Pro Ser Ser Arg Glu Ala Gly Arg
625                 630                 635

<210> SEQ ID NO 7
<211> LENGTH: 445
<212> TYPE: DNA
<213> ORGANISM: Artificial Sequence
<220> FEATURE:
<223> OTHER INFORMATION: Description of Artificial Sequence:Nucleotide
      sequence of a portion of the PERV-A env gene
      corresponding to nucleotides 364-809 of GenBank
      No. Y12238.

<400> SEQUENCE: 7
cccataaacc cttatctctc acctggttac ttactgactc cggtacaggt attaatatta      60
acagcactca aggggaggct cccttgggga cctggtggcc tgaattatat gtctgccttc     120
gatcagtaat ccctggtctc aatgaccagg ccacaccccc cgatgtactc cgtgcttacg     180
ggttttacgt ttgcccagga ccccaaata atgaagaata ttgtggaaat cctcaggatt     240
tcttttgcaa gcaatggagc tgcataactt ctaatgatga ggaattggaa atggccagtc     300
tctcagcaag acagagtaag ttactctttt gttaacaatc ctaccagtta taatcaattt     360
aattatggcc atgggagatg gaaagattgg caacagcggg tacaaaaaga tgtacgaaat     420
aagcaaataa gctgtcaatt cgtta                                          445

```
<210> SEQ ID NO 8
<211> LENGTH: 276
<212> TYPE: DNA
<213> ORGANISM: Artificial Sequence
<220> FEATURE:
<223> OTHER INFORMATION: Description of Artificial Sequence:Nucleotide
      sequence of part of PERV-B env gene corresponding
      to residues 1350-1623 of GenBank Accession No.
      Y12239.

<400> SEQUENCE: 8
gccgatctct ctccaggacc gggtaaaatt ctcctttgtc aattccggcc cgggcaagta     60
caaagtgatg aaactatata agataagag  ctgctcccca tcagacttag attatctaaa    120
gataagtttc actgaaaaag gaaaacagga aaatattcaa aagtggataa atggtatgag    180
ctggggaata gttttttata aatatggcgg gggagcaggg tccactttaa ccattcgcct    240
taggatagag acggggacag aaccccctgt ggcagt                              276

<210> SEQ ID NO 9
<211> LENGTH: 288
<212> TYPE: DNA
<213> ORGANISM: Artificial Sequence
<220> FEATURE:
<223> OTHER INFORMATION: Description of Artificial Sequence:Nucleotide
      sequence of part of PERV-C env gene corresponding
      to GenBank Accession No. AF038600.

<400> SEQUENCE: 9
gccaacctct cagcaggata gggtaagttt ttcttatgtc aacacctata ccagctctgg     60
acaatttaat tacctgacct ggattagaac tggaagcccc aagtgctctc cttcagacct    120
agattaccta aaaataagtt tcactgagaa aggaaaacaa gaaatatcc  taaaatgggt    180 aaatggtatg tcttggggaa tggtatatta tggaggctcg ggtaaacaac caggctccat    240
tctaactatt cgcctcaaaa taaaccagct ggagcctcca atggctat                 288

<210> SEQ ID NO 10
<211> LENGTH: 278
<212> TYPE: DNA
<213> ORGANISM: Artificial Sequence
<220> FEATURE:
<223> OTHER INFORMATION: Description of Artificial Sequence:Nucleotide
      sequence of part of PoEV env gene corresponding to
      residues 6057-6333 of WO 97/40167 for comparison.

<400> SEQUENCE: 10
gccgatctct ctccaggacc gggtaaaatt ctcctttgtc aattccggcc cgggcaagta     60
caaaatgatg aaactatata agataagag  ctgctcccca tcagacttag attatctaaa    120
gataagtttc actgaaagga aaacaggaaa atattcaaaa gtggataaat ggtatgagct    180
ggggaatagt tttttattat atggcggggg agcagggtcc actttaacca ttcgccttag    240
gatagagacg gggacagaac ccctgtggc  aatgggac                            278

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence:PCR forward
      primer sequence.

<400> SEQUENCE: 11
gccaacctct cagcaggata g                                               21
```

```
<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:PCR reverse
      primer sequence.

<400> SEQUENCE: 12
atagccattg gaggctccag                                                    20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:PCR forward
      primer DA111.

<400> SEQUENCE: 13
caccaacggc tgtgaaagtc                                                    20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:PCR forward
      primer DA185.

<400> SEQUENCE: 14
tctcgtactt ttgaccacac                                                    20

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence:PCR reverse
      primer PERV-D-R2 that binds to the reverse of
      residues 200-218 of SEQ ID NO: 1.

<400> SEQUENCE: 15
 ggttgtctgt cccaacctg                                                    19

<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence:PCR forward
      primer M13F.

<400> SEQUENCE: 16
gtaaaacgac ggccag                                                        16

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence:PCR reverse
      primer M13R.

<400> SEQUENCE: 17
caggaaacag ctatgac                                                       17
```

```
<210> SEQ ID NO 18
<211> LENGTH: 698
<212> TYPE: DNA
<213> ORGANISM: Artificial Sequence
<220> FEATURE:
<223> OTHER INFORMATION: Description of Artificial Sequence:Sequence of a
      5' env fragment of PERV-D.

<400> SEQUENCE: 18
caccaacggc tgtgaaagtc gaaaaaatct ccacctagat ccatacatcc cacgttaagc      60
cggcgccacc tcctgattca gggtgaaaag ccaaaaagac taaaaatccc cttaagcttc     120
gcctccatca catggttcct tactctgtca ataacctctc agactaatgg tatgcacata     180
ggagacagcc tgaactccca taaaccctta tctctgacct ggttaattac tgactctgac     240
acaggtatta atatncacag cgctcgaggg gaggctcctt tagaaacctg gtggcctgat     300
ctatatgtct gcctcagatc agtcattcct agtctgacct caaccccaga tatcctccgt     360
gcttacggat tttatgtttg cccaggacca ccaaataatg gaaaacacta tggaaatcct     420
agagatttct tttacaaaca atggagctgt gtaacctcta atgatggaaa tcgaaaatgg     480
ccaacctctc tgcaggatag ggtaagcttt tcttatgtca accccaataa ccaccggacc     540
tggaaaacgt catacaggta ccattctggg tgttttccct cagacctaga ttatcttaaa     600
ataagtttca ccgaaaaaaa aaaacaagaa aatatcctaa aatggataaa tggtatgtcc     660
tggggaataa tatattatac aggttgggac agacaacc                             698

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence:PCR forward
      primer corresponding to reverse of PERV-C
      nucleotides 6475-6493 in GneBank Accession No.
      AF038600.

<400> SEQUENCE: 19
gaaaagctcc ctggatgag                                                   19

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence:PCR primer
      for PERV-D F1 corresponding to nucleotides 548-568 of
      SEQ ID NO: 18.

<400> SEQUENCE: 20
gtcatacagg taccattctg g                                                21

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:PCR primer
      corresponding to nucleotides 517-536 of SEQ ID
      NO:18.

<400> SEQUENCE: 21
gtcaacccca ataaccaccg                                                  20
```

<210> SEQ ID NO 22
<211> LENGTH: 349
<212> TYPE: DNA
<213> ORGANISM: Artificial Sequence
<220> FEATURE:
<223> OTHER INFORMATION: Description of Artificial Sequence:Sequence
    derived from extending sequence analysis into the
    proline rich region of PERV-D env region.

<400> SEQUENCE: 22
gtcatacagg taccattctg ggtgttttcc ctcagaccta gattatctta aaataagttt     60
caccgaaaaa aaaaaacaag aanatatcct aaaatggata atggtatgt cctggggaat    120 aatatattat acaggttggg acagacaacc aggctccatt ctaaccatcc gacttaaaat    180
aagccagcta gagcctccaa tggctatagg ccgaatacgg tcttaacggg tcaaagaacc    240
ccaaccccag gaccatcctc tgatataact tctaaattag accccactga gtctaactgc    300
acgactaaaa cgggnacaaa acttttttagt ctcatccagg gagcttttc                349

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence:PCR primer
    DA189.

<400> SEQUENCE: 23
ttttcatcct ttcattcccc acttc                                            25

<210> SEQ ID NO 24
<211> LENGTH: 1493
<212> TYPE: DNA
<213> ORGANISM: Artificial Sequence
<220> FEATURE:
<223> OTHER INFORMATION: Description of Artificial Sequence:Nucleotide
    sequence of the 3' end of the PERV-D env region.

<400> SEQUENCE: 24
aaccccaata accaccggac ctggaaaacg tcatacaggt accattctgg gtgttttccc     60
tcagacctag attatcttaa aataagtttc accgaaaaaa aaaaacaaga aaatatccta    120
aaatggataa atggtatgtc ctggggaata atatattata caggttggga cagacaacca    180
ggctccattc taaccatccg acttaaaata agccagctag agcctccaat ggctatagga    240
ccgaatacgg tcttaacggg tcaaagaacc ccaaccccag gaccatcctc tgatataact    300
tctaaattag accccactga gtctaacagc acgactaaaa cggggacaaa acttttttagt    360 ctcatccagg gagcttttca agctcttaac tccacgactc cagaggctac ctcttcttgt    420
tggctttgct taacttcggg cccaccttac tataagaaaa tggctaaaag agaaaaattc    480
aatgtgacaa aaaacatag agaccaatgt acatggggat cccaaaataa gcttacccctt    540 actgaggttt ctggaaagga cacctgcata aaaaggttc ccccatccca ccaacacctt    600
tacaaccaca ctgaagcctt taatcaaacc tctgagagtc aatatctggt acctggttat    660
gacaggtggt gggcatgtaa tactggatta accccttgtg tttccacctt ggttttcaac    720
caaactaaag acttttacat tatggtccaa attgttcccc gagtatatta ctatcccaag    780
aaaacaattc tcgatgaata tgattacagg aaccatcgac aaaagaaaaa acccatatcc    840 ctgcacactcg cagtaatgct cggactcgga gtgataacag gtgtgagaac aggaactgca    900 gcttttagtta caggacctca gcagctagaa acaggactta gtaacctaca tcaaattgta    960

-continued

```
acaggaaatc tccaagccct aaaaaaatct gtcagtaacc tggaaaaatc cctaacctcc      1020
ttatctgaag tagttctaca gaataaaaaa gggttagatt tattatttct aaaaaaaaga      1080
agattatgtg tagccttaaa ggagaaatgc tgtttttatg tagatcattc aggggccatc      1140
agagactcca tgaacaagct taaaaaaagg ttggagaaac gtcgaaggga aaggaaact       1200 tactcaaaga tggtttaaaa gatggttcaa caggtctcct tggttggcta ccctactttc      1260
tactttaaca ggacccttaa tagtcctcct cctgttactc acagttgggc catgtattat      1320
taacaagtta attgccttca ttagaaaacg aataagtgca gtccagatca tggtacttag      1380
acaacagtac caaaacccat ctaacaggga agctggccgc tagctctacc agttctaaga     1440
ttaaaactat taacaagaga agaagtgggg aatgaaagga taagggcgaa ttc             1493
```

<210> SEQ ID NO 25
<211> LENGTH: 2000
<212> TYPE: DNA
<213> ORGANISM: Artificial Sequence
<220> FEATURE:
<223> OTHER INFORMATION: Description of Artificial Sequence:Contiguous
      compilation of SEQ ID NOs: 18, 22, and 24.

<400> SEQUENCE: 25

```
caccaacggc tgtgaaagtc gaaaaaatct ccacctagat ccatacatcc cacgttaagc       60
cggcgccacc tcctgattca gggtgaaaag ccaaaaagac taaaaatccc cttaagcttc      120
gcctccatca catggttcct tactctgtca ataacctctc agactaatgg tatgcacata      180
ggagacagcc tgaactccca taaacccttta tctctgacct ggttaattac tgactctgac    240
acaggtatta atatccacag cgctcgaggg gaggctcctt tagaaacctg gtggcctgat      300
ctatatgtct gcctcagatc agtcattcct agtctgacct caaccccaga tatcctccgt      360
gcttacggat tttatgtttg cccaggacca ccaaataatg gaaaacacta tggaaatcct      420
agagatttct tttacaaaca atggagctgt gtaacctcta atgatggaaa tcgaaaatgg      480
ccaacctctc tgcaggatag ggtaagcttt tcttatgtca accccaataa ccaccggacc      540
tggaaaacgt catacaggta ccattctggg tgttttccct cagacctaga ttatcttaaa      600
ataagtttca ccgaaaaaaa aaaacaagaa aatatcctaa aatggataaa tggtatgtcc      660
tggggaataa tatattatac aggttgggac agacaaccag gctccattct aaccatccga      720
cttaaaataa gccagctaga gcctccaatg gctataggac cgaatacggt cttaacgggt      780
caaagaaccc caacccccagg accatcctct gatataactt ctaaattaga ccccactgag     840
tctaacagca cgactaaaac ggggacaaaa cttttttagtc tcatccaggg agcttttcaa      900
gctcctaact ccacgactcc agaggctacc tcttcttgtt ggctttgctt aacttcgggc      960
ccaccttact ataagaaaat ggctaaaaga gaaaaattca atgtgacaaa aaaacataga     1020
gaccaatgta catggggatc ccaaaataag cttacccttaa ctgaggtttc tggaaaggac    1080
acctgcataa aaaaggttcc cccatcccac caacacccttt acaaccacac tgaagccttt   1140
aatcaaacct ctgagagtca atatctggta cctggttatg acaggtggtg ggcatgtaat    1200
actggattaa ccccttgtgt ttccacctg gttttcaacc aaactaaaga cttttacatt    1260
atggtccaaa ttgttccccg agtatattac tatcccaaga aaacaattct cgatgaatat   1320
gattacagga accatcgaca aaagaaaaaa cccatatccc tgacactcgc agtaatgctc    1380
ggactcggag tgataacagg tgtgagaaca ggaactgcag ctttagttac aggacctcag    1440
cagctagaaa caggacttag taacctacat caaattgtaa caggaaatct ccaagcccta    1500
```

```
aaaaaatctg tcagtaacct ggaaaaatcc ctaacctcct tatctgaagt agttctacag    1560
aataaaaaag ggttagattt attatttcta aaaaaaagaa gattatgtgt agccttaaag    1620
gagaaatgct gttttttatgt agatcattca ggggccatca gagactccat gaacaagctt    1680
aaaaaaaggt tggagaaacg tcgaagggaa aaggaaactt actcaaagat ggtttaaaag    1740
atggttcaac aggtctcctt ggttggctac cctactttct actttaacag gacccttaat    1800
agtcctcctc ctgttactca cagttgggcc atgtattatt aacaagttaa ttgccttcat    1860
tagaaaacga ataagtgcag tccagatcat ggtacttaga caacagtacc aaaacccatc    1920
taacagggaa gctggccgct agctctacca gttctaagat taaaactatt aacaagagaa    1980
gaagtgggga atgaaaggat                                                 2000
```

```
<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence:PCR primer
      PERV-Dpol-F.

<400> SEQUENCE: 26
aacggctgtg aaagtcgaaa a                                                21

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence:PCR primer
      DA176.

<400> SEQUENCE: 27
caccacctgt cataaccagg tacc                                             24

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence:PCR primer
      DA158.

<400> SEQUENCE: 28
agtagtttcc ttttcccttc gacgcttc                                         28

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence:PCR primer
      DA47.

<400> SEQUENCE: 29
cgccagggtt tcccagtcac gac                                              23

<210> SEQ ID NO 30
<211> LENGTH: 2000
<212> TYPE: DNA
<213> ORGANISM: Artificial Sequence
<220> FEATURE:
<223> OTHER INFORMATION: Description of Artificial Sequence:Nucleotide
      consensus sequence of PERV-D.
```

<400> SEQUENCE: 30

```
caccaacggc tgtgaaagtc gaaaaaatct ccacctagat ccatacatcc cacgttaagc      60
cggcgccacc tcctgattca gggtgaaaag ccaaaaagac taaaaatccc cttaagcttc     120
gcctccatca catggttcct tactctgtca ataacctctc agactaatgg tatgcacata     180
ggagacagcc tgaactccca taaacccta tctctgacct ggttaattac tgactctgac      240
acaggtatta atatccacag cgctcgaggg gaggctcctt tagaaacctg gtggcctgat     300
ctatatgtct gcctcagatc agtcattcct agtctgacct caaccccaga tatcctccgt     360
gcttacggat tttatgtttg cccaggacca ccaaataatg gaaaacacta tggaaatcct     420
agagatttct tttacaaaca atggagctgt gtaacctcta atgatggaaa tcgaaaatgg     480
ccaacctctc tgcaggatag ggtaagcttt tcttatgtca accccaataa ccaccggacc     540
tggaaaacgt catacaggta ccattctggg tgttttccct cagacctaga ttatcttaaa     600
ataagtttca ccgaaaaaaa aaacaagaa aatatcctaa aatggataaa tggtatgtcc       660
tgggaataa tatattatac aggttgggac agacaaccag gctccattct aaccatccga       720
cttaaaataa gccagctaga gcctccaatg gctataggac cgaatacggt cttaacgggt     780
caaagaaccc caaccccagg accatcctct gatataactt ctaaattaga ccccactgag     840
tctaacagca cgactaaaac ggggacaaaa ctttttagtc tcatccaggg agcttttcaa     900
gctcctaact ccacgactcc agaggctacc tcttcttgtt ggctttgctt aacttcgggc     960
ccaccttact ataagaaaat ggctaaaaga gaaaaattca atgtgacaaa aaacataga     1020
gaccaatgta catggggatc ccaaaataag cttacccctta ctgaggtttc tggaaaggac   1080
acctgcataa aaaaggttcc cccatcccac caacaccttt acaaccacac tgaagccttt    1140
aatcaaacct ctgagagtca atatctggta cctggttatg acaggtggtg ggcatgtaat    1200
actggattaa ccccttgtgt ttccaccttg gttttcaacc aaactaaaga cttttacatt    1260
atggtccaaa ttgttccccg agtatattac tatcccaaga aaacaattct cgatgaatat    1320
gattacagga accatcgaca aaagaaaaaa cccatatccc tgacactcgc agtaatgctc    1380
ggactcggag tgataacagg tgtgagaaca ggaactgcag ctttagttac aggacctcag    1440
cagctagaaa caggacttag taacctacat caaattgtaa caggaaatct ccaagccta     1500
aaaaaatctg tcagtaacct ggaaaaatcc ctaacctcct tatctgaagt agttctacag    1560
aataaaaaag ggttagattt attatttcta aaaaaaagaa gattatgtgt agccttaaag    1620
gagaaatgct gttttttatgt agatcattca ggggccatca gagactccat gaacaagctt    1680
aaaaaaggt tggagaaacg tcgaagggaa aaggaaactt actcaaagat ggtttaaaag    1740
atggttcaac aggtctcctt ggttggctac cctactttct actttaacag gacccttaat    1800
agtcctcctc ctgttactca cagttgggcc atgtattatt aacaagttaa ttgccttcat    1860
tagaaaacga ataagtgcag tccagatcat ggtacttaga caacagtacc aaaacccatc    1920
taacagggaa gctggccgct agctctacca gttctaagat taaaactatt aacaagagaa    1980
gaagtgggga atgaaaggat                                                 2000
```

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence:PERV-D specific PCR primer ALR-4.

-continued

```
<400> SEQUENCE: 31
cggtggttat tggggttgac                                              20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence:PERV-C/D
      specific PCR primer corresponding to nucleotides
      6100-6120 of GenBank Accession No. AF038600.

<400> SEQUENCE: 32
ccaacctctc tgcaggatag                                              20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence:PERV-C/D
      specific primer for PCR amplification.

<400> SEQUENCE: 33
atagccattg gaggctccag                                              20
```